United States Patent
Skov

(10) Patent No.: US 6,548,479 B1
(45) Date of Patent: Apr. 15, 2003

(54) THERAPEUTIC USES OF DEPSIPEPTIDES AND CONGENERS THEREOF

(75) Inventor: Søren Skov, Copenhagen (DK)

(73) Assignee: Xcyte Therapies, Inc., Seattle, WA (US)

( * ) Notice: Subject to any disclaimer, the term of this patent is extended or adjusted under 35 U.S.C. 154(b) by 0 days.

(21) Appl. No.: 10/115,576

(22) Filed: Apr. 2, 2002

Related U.S. Application Data

(63) Continuation of application No. 09/732,183, filed on Dec. 6, 2000, now Pat. No. 6,403,555.
(60) Provisional application No. 60/193,582, filed on Mar. 30, 2000, and provisional application No. 60/169,731, filed on Dec. 8, 1999.

(51) Int. Cl.$^7$ .................. A61K 37/02; A61K 38/08; C07K 5/08; C07K 7/06

(52) U.S. Cl. .................. 514/10; 514/18; 514/19; 530/317; 530/323; 530/330; 530/331

(58) Field of Search .................. 514/10, 18, 19; 530/317, 323, 330, 331

(56) References Cited

U.S. PATENT DOCUMENTS

| | | | |
|---|---|---|---|
| 4,268,516 A | 5/1981 | Lombardino et al. | 424/273 P |
| 4,977,138 A | 12/1990 | Okuhara et al. | 514/10 |
| 5,294,603 A | 3/1994 | Rinehart | 514/10 |
| 5,591,717 A | 1/1997 | Rojko et al. | 514/12 |
| 5,843,943 A | 12/1998 | Carson et al. | 514/249 |
| 5,891,653 A | 4/1999 | Attfield | 435/7.21 |
| 5,942,229 A | 8/1999 | Noelle et al. | 424/154.1 |
| 6,211,145 B1 | 4/2001 | Yanai et al. | 514/10 |
| 6,252,041 B1 | 6/2001 | Yanai et al. | 530/331 |
| 6,265,537 B1 | 7/2001 | Jeschke et al. | 530/317 |
| 6,316,406 B1 | 11/2001 | Yanai et al. | 514/11 |

FOREIGN PATENT DOCUMENTS

| | | |
|---|---|---|
| EP | 352 646 B1 | 6/1993 |
| EP | 931 544 A2 | 7/1999 |
| WO | WO 93/19778 | 10/1993 |
| WO | WO 95/33823 | 12/1995 |
| WO | WO 97/35990 | 10/1997 |
| WO | WO 98/39412 | 9/1998 |
| WO | WO 98/46640 | 10/1998 |
| WO | WO 99/11659 | 3/1999 |
| WO | WO 99/14241 | 3/1999 |
| WO | WO 99/15174 | 4/1999 |
| WO | WO 99/20296 | 4/1999 |
| WO | WO 99/25703 | 5/1999 |
| WO | WO 99/30730 | 6/1999 |
| WO | WO 99/51731 | 10/1999 |

OTHER PUBLICATIONS

Agrawal and Reynolds, "An Evaluation of the Mitogenic Reactivity of Intestinal Intraepithelial Lymphocytes of Chickens," *Avian Diseases* 43: 172–181, 1999.

Aramburu et al., "Affinity–Driven Peptide Selection of an NFAT Inhibitor More Selective Than Cyclosporin A," *Science* 285: 2129–2133, Sep. 24, 1999.

Bierer et al., "Cyclosporin A and FK506: molecular mechanisms of immunosuppression and probes for transplantation biology," *Current Opinion in Immunology* 5: 763–773, 1993.

Blyth et al., "Lung Inflammation and Epithelial Changes in a Murine Model of Atopic Asthma," *Am. J. Respir. Cell Mol. Biol.* 14: 425–438, 1996.

Böhmig et al., "n–Butyrate downregulates the stimulatory function of peripheral blood–derived antigen–presenting cells: a potential mechanism for modulating T–cell responses by short–chain fatty acids," *Immunology* 92: 234–243, 1997.

Bonneville et al., "Self–tolerance to transgenic γδ T cells by intrathymic inactivation," *Nature* 344: 163–165, Mar. 8, 1990.

Bottazzo et al., "In Situ Characterization of Autoimmune Phenomena and Expression of HLA Molecules in the Pancreas in Diabetic Insulitis," *The New England Journal of Medicine* 313(6): 353–360, Aug. 8, 1985.

Byrd et al., "Depsipeptide (FR901228): A Novel Therapeutic Agent With Selective, In Vitro Activity Against Human B–Cell Chronic Lymphocytic Leukemia Cells," *Blood* 94(4): 1401–1408, Aug. 15, 1999.

(List continued on next page.)

*Primary Examiner*—Deborah C. Lambkin
(74) *Attorney, Agent, or Firm*—Seed Intellectual Property Law Group PLLC

(57) ABSTRACT

Depsipeptides and congeners thereof are disclosed having the following structure:

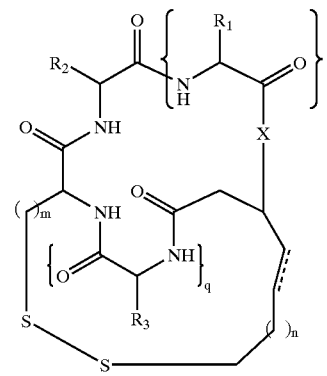

wherein m, n, p, q, X, $R_1$, $R_2$ and $R_3$ are as defined herein. These compounds, including FR901228, have activity as, for example, immunosuppressants, as well as for the prevention or treatment of patients suffering or at risk of suffering from inflammatory, autoimmune or immune system-related diseases including graft-versus-host disease and enhancement of graft/tissue survival following transplant. Also provided are methods for inhibiting lymphocyte activation, proliferation, and/or suppression of IL-2 secretion.

12 Claims, 10 Drawing Sheets

OTHER PUBLICATIONS

Cantrell and Smith, "The Interleukin–2 T–Cell System: A New Cell Growth Model," *Science 224*: 1312–1316, Jun. 22, 1984.

Chan et al., "Depsipeptide (FR901228, NSC–630176) pharmacokinetics in the rat by LC/MS/MS," *Investigational New Drugs 15*: 195–206, 1997.

Chassaing et al., "Determination of the antitumor agent depsipeptide in plasma by liquid chromatography on serial octadecyl stationary phases," *Journal of Chromatography B 719*: 169–176, 1998.

Dangond et al., "Differential Display Cloning of a Novel Human Histone Deacetylase (HDAC3) cDNA from PH–Activated Immune Cells," *Biochemical and Biophysical Research Communications 242*: 648–652, 1998.

Dangond and Gullans, "Differential Expression of Human Histone Deacetylase mRNAs in Response to Immune Cell Apoptosis Induction by Trichostatin A and Butyrate," *Biochemical and Biophysical Research Communications 247*: 833–837, 1998.

Dengler et al., "Development of a propidium iodile fluorescence assay for proliferation and cytotoxicity assays," *Anti-Cancer Drugs 6*: 522–532, 1995.

Dent et al., "Self–reactive γδ T cells are eliminated in the thymus," *Nature 343*: 714–719, Feb. 22, 1990.

Eisenberg et al., "Male Determined Accelerated Autoimmune Disease in BXSB Mice: Transfer by Bone Marrow and Spleen Cells," *The Journal of Immunology 125*(3): 1032–1036, Sep. 1980.

Espinos et al., "Cooperation between Phosphorylation and Acetylation Processes in Transcriptional Control," *Molecular and Cellular Biology 19*(5): 3474–3484, May 1999.

Espinos and Weber, "Activation of the MAP kinase cascade by histone deacetylase inhibitors is required for the stimulation of choline acetyltransferase gene promoter," *Molecular Brain Research 56*: 118–124, 1998.

Farrar et al., "Regulation of the Production of Immune Interferon and Cytotoxic T Lymphocytes by Interleukin 2," *The Journal of Immunology 126*(3): 1120–1125, Mar. 1981.

Ferguson and Green, "T cells are just dying to accept grafts," *Nature Medicine 5*(11): 1231–1232, Nov. 1999.

Finnin et al., "Structures of a histone deacetylase homologue bound to the TSA and SAHA inhibitors," *Nature 401*: 188–193, Sep. 9, 1999.

Geller, R.L., "Role of Cross–Linking in Stepwise Activation of T Cells," *Scand. J. Immunol. 35*: 327–334, 1992.

Grewal and Flavell, "CD40 and CD154 in Cell–Mediated Immunity," *Annu. Rev. Immunol. 16*: 111–135, 1998.

Grozinger et al., "Three proteins define a class of human histone deacetylases related to yeast Hdalp," *Proc. Natl. Acad. Sci. USA 96*: 4868–4873, 1999.

Hara et al., "Human T Cell Activation II. A New Activation Pathway Used by a Major T Cell Population Via a Disulfide–bonded Dimer of a 44 Kilodalton Polypeptide (9.3 Antigen)," *J. Exp. Med. 161*: 1513–1524, Jun. 1985.

Harding et al., "CD28–mediated signaling co–stimulates murine T cells and prevents induction of anergy in T–cell clones," *Nature 356*: 607–609, Apr. 16, 1992.

Hassig et al., "A role for histone deacetylase activity in HDAC1–medaited transcriptional repression," *Proc. Natl. Acad. Sci. USA 95*: 3519–3524, Mar. 1998.

Henderson et al., "Comparison of the effects of FK–506, cyclosporin A and rapamycin on IL–2 production," *Immunololgy 73*: 316–321, 1991.

Hojo et al., "Cyclosporin induces cancer progression by a cell–autonomous mechanism," *Nature 397*: 530–534, Feb. 11, 1999.

Holtrop et al., "Removal of monocytes from cell suspensions with anti–CD14 antibody and carbonyl–iron, using FcγR–dependent accessory function as a sensitive measure of monocyte presence," *Journal of Immunological Methods 156*: 217–222, 1992.

Hu et al., "Kinetics of interferon–γ secretion and its regulatory factors in the early phase of acute graft–versus–host disease," *Immunology 98*: 379–385, 1999.

Huang and Kadonaga, "Biochemical Analysis of Transcriptional Repression by Drosophila Histone Deacetylase 1," *J. Biol. Chem. 276*(16): 12497–12500, Apr. 2001.

Isoniemi, H., "New Trends in Maintenance Immunosuppression," *Annales Chirurgiae et Gynaecologiae 86*(2): 164–170, 1997.

Kaufman et al., "Xenotransplantation," *Annu. Rev. Immunol. 13*: 339–367, 1995.

Kelley et al., "Cloned Human Interferon–γ, But Not Interferon–β or –α, Induces Expression of HLA–DR Determinants by Fetal Monocytes and Myeloid Leukemic Cell Lines," *The Journal of Immunology 132*(1): 240–245, Jan. 1984.

Kim et al., "Mechanism of Cell Cycle Arrest Caused by Histone Deacetylase Inhibitors in Human Carcinoma Cells," *J. Antibiot. (Tokyo) 53*(10): 1191–1200, Oct. 2000.

Kitazono et al., "Construction of Gene Therapy Vectors Targeting Thyroid Cells: Enhancement of Activity and Specificity with Histone Deacetylase Inhibitors and Agents Modulating the Cyclic Adenosine 3', 5'–Monophosphate Pathway and Demonstration of Activity in Follicular and Anaplastic Thyroid Carcinoma Cells," *J. Clin. Endocrinol. Metab. 86*(2): 834–840, Feb. 2001.

Kobashigawa, J.A., "Controversies in Heart and Lung Transplantation Immunosuppression: Tacrolimus Versus Cyclosporine," *Transplantation Proceedings 30*: 1095–1097, 1998.

Kohge et al., "Promotion of Antigen–specific Antibody Production in Murine B Cells by a Moderate Increase in Histone Acetylation," *Biochemical Pharmacology 56*: 1359–1364, 1998.

Komatsu and Hayashi, "Histone Deacetylase Inhibitors Up–regulate the Expression of Cell Surface MHC Class–I Molecules in B16/BL6 Cells," *The Journal of Antibiotics 51*(1): 89–91, Jan. 1998.

Kosugi et al., "In vivo Effects of a Histone Deacetylase Inhibitor, FK228, on Human Acute Promyelocytic Leukemia in NOD/Shi–scid/scid Mice," *Jpn. J. Cancer Res. 92*(5): 529–536, May 2001.

Kubota et al., "Interferons Alpha–2a and Beta Increase the Antitumor Activity, Detected by MTT Assay, of 5–Fluorouracil against Experimental and Clinical Human Gastrointestinal Carcinomas," *Anticancer Research 17*: 725–728, 1997.

Kwon et al., "Depudecin induces morphological reversion of transformed fibroblasts via the inhibition of histone deacetylase," *Proc. Natl. Acad. Sci. USA 95*: 3356–3361, 1998.

Levine et al., "CD28 ligands CD80 (B7–1) and CD86 (B7–2) induce long–term autocrine growth of CD4+ T cells and induce similar patterns of cytokine secretion in vitro," *International Immunology 7*(6): 891–904, 1995.

Li et al., "Total Synthesis of the Antihumor Depsipeptide FR–901,228," *J. Am. Chem. Soc. 118*(30): 7237–7238, 1996.

Linsley et al., "Immunosuppression in Vivo by a Soluble Form of the CTLA–4 T Cell Activation Molecule," *Science* 257: 792–795, Aug. 7, 1992.

Liu et al., "Calcineurin Is a Common Target of Cyclophilin–Cyclosporin A and FKBP–FK506 complexes," *Cell 66*: 807–815, Aug. 23, 1991.

Mackey et al., "The role of CD40/CD154 interactions in the priming, differentiation, and effector function of helper and cytotoxic T cells," *Journal of Leukocyte Biology 63*: 418–428, Apr. 1998.

Maeda et al., "Up–regulation of costimulatory/adhesion molecules by histone deacetylase inhibitors in acute myeloid leukemia cells," *Blood 96*(12): 3847–3856, Dec. 1, 2000.

Makino et al., "Breeding of a Non–Obese, Diabetic Strain of Mice," *Exp. Anim. 29*(1): 1–13, 1980.

Miller, E., "Immunosuppression–An Overview," *Seminars in Veternary Medicine and Surgery (Small Animal) 12*(3): 144–149, Aug. 1997.

Miyazaki et al., "Predominance of T lymphocytes in pancreatic islets and spleen of pre–diabetic non–obese diabetic (NOD) mice: a longitudinal study," *Clin. Exp. Immunol. 60*: 622–630, 1985.

Mookerjee and Ballard, "Functional Characteristics of Monocytes 1. Essential Role in the Transformational Response of Human Blood Lymphocytes to Phytomitogens," *Transplantation 23*(1): 22–28, Jan. 1977.

Morris et al., "Experimental Induction of Systemic Lupus Erythematosus by Recognition of Foreign Ia," *Clinical Immunology and Immunopathology 57*: 263–273, 1990.

Murata et al., "Apoptotic Cytotoxic Effects of a Histone Deacetylase Inhibitor, FK228, on Malignant Lymphoid Cells," *Jpn. J. Cancer Res. 91*(11): 1154–1160, Nov. 2000.

Nakajima et al., "FR901228, a Potent Antitumor Antibiotic, Is a Novel Histone Deacetylase Inhibitor," *Experimental Cell Research 241*: 126–133, 1998.

Pankewycz et al., "Interleukin–2–Diphtheria Toxin Fusion Protein Prolongs Murine Islet Cell Engraftment," *Transplantation 47*(2): 318–322, Feb. 1989.

Philip and Gerson, "Toxicology and Adverse Effects of Drugs Used For Immunosuppression in Organ Transplantation," *Toxicology 18*(4): 755–765, Dec. 1998.

Pober et al., "Ia Expression by Vascular Endothelium is Inducible by Activated T Cells and by Human γ Interferon," *J. Exp. Med. 157*: 1339–1353, Apr. 1983.

Rajgolikar et al., "Effects of a novel antitumor depsipeptide, FR901228, on human breast cancer cells," *Breast Cancer Research and Treatment 51*: 29–38, 1998.

Richards et al., "Phase I Evaluation of Humanized OKT3: Toxicity and Immunomodulatory Effects of hOKT3$\gamma_4$," *Cancer Research 59*: 2096–2101, May 1, 1999.

Strom, T.B., "Immunosuppressive Treatments That Thwart Transplant Rejection," *Clinical Aspects of Autoimmunity 4*(3): 8–19, 1990.

Takahashi et al., "Generalized Lymphoproliferative Disease in Mice, Caused by a Point Mutation in the Fas Ligand," *Cell 76*: 969–976, Mar. 25, 1994.

Takakura et al., "An in vivo model of human skin acute graft–versus–host disease: transplantation of cultured human epidermal cells and dermal fibroblasts with human lymphocytes into SCID mice," *Experimental Hematology 27*: 1815–1821, 1999.

Theofilopoulos and Dixon, "Murine Models of Systemic Lupus Erythematosus," *Advances in Immunology 37*: 269–391, 1985.

Todd et al., "Genetic analysis of autoimmune type 1 diabetes mellitus in mice," *Nature 351*: 542–547, Jun. 13, 1991.

Ueda et al., "FR901228, A Novel Antitumor Bicyclic Depsipeptide Produced by *Chromobacterium violaceum* No. 968 III. Antitumor Activities on Experimental Tumors in Mice," *The Journal of Antibiotics 47*(3): 315–323, 1993.

Van Lint et al., "The Expression of a Small Fraction of Cellular Genes Is Changed in Response to Histone Hyperacetylation," *Gene Expression 5*: 245–253, 1996.

Vos and Van Loveren, "Experimental studies on immunosuppression: how do they predict for man?," *Toxicology 129*: 13–26, 1998.

Wang et al., "Fungal metabolite FR901228 inhibits c–Myc and Fas ligand expression," *Oncogene 17*: 1503–1508, 1998.

Watanabe et al., "A Molecular Genetic Linkage Map of Mouse Chromosome 19, Including the lpr, Ly–44, and Tdt Genes," *Biochemical Genetics 29*(7/8): 325–335, 1991.

Weiser et al., "Induction of MAGE–3 Expression in Lung and Esophageal Cancer Cells," *Ann. Thorac. Surg. 71*(1): 295–302, Jan. 2001.

Weiser et al., "Sequential 5–Aza–2'–deoxycytidine–Depsipeptide FR901228 Treatment Induces Apoptosis Preferentially in Cancer Cells and Facilitates Their Recognition by Cytolytic T Lymphocytes Specific for NY–ESO–1" *J. Immunother. 24*(2): 151–161, Mar. 2001.

Williams et al., "Dual Parameter Flow Cytometric Analysis of DNA Content, Activation Antigen Expression, and T Cell Subset Proliferation in the human Mixed Lymphocyte Reaction," *The Journal of Immunology 132*(5): 2330–2337, May 1984.

Effect of FR901228 on lymphocyte activation markers

THERAPEUTIC USES OF DEPSIPEPTIDES AND CONGENERS THEREOF

CROSS REFERENCE TO RELATED APPLICATIONS

This application is a CON of Ser. No. 09/732,183 Dec. 6, 2000 U.S. Pat. No. 6,403,555, which claims priority to U.S. Provisional Application No. 60/169,731, filed on Dec. 8, 1999 and U.S. Provisional Application No. 60/193,582, filed Mar. 30, 2000.

TECHNICAL FIELD

The present invention relates generally to depsipeptides or congeners thereof and use of the same as an immunosuppressant and, more specifically, to the treatment and/or prevention of an immune disorder such as autoimmune or inflammatory diseases, and for reducing immunorejection of transplanted material, by administering to an animal an effective amount of a depsipeptide such as FR901228.

BACKGROUND OF THE INVENTION

Modulation of the immune system is desirous in a variety of contexts, from inhibiting an autoimmune response, to controlling infectious disease and inhibiting graft/tissue rejection. The principal approach to mitigate rejection is the pharmacological suppression of the immune system of the recipient. With this in mind, most immunomodulatory compounds that are currently utilized are immunosuppressive. Since the early 1960's the availability of these immunosuppressive agents have been restricted to only a few drugs. However, in the early 1980's in addition to azathioprine and corticosteroids, cyclosporine became widely available and has been the drug of choice ever since. (Kobashigawa, *Trans. Proc.* 30:1095–1097, 1998; Isoniemi, *Ann. Chi. Gyn.* 86:164–170, 1997). However, the newer immunosuppressive agents are relatively few in number and also suffer from many of the undesirable side-effects associated with earlier agents. While these drugs have been used to increase survival times for transplanted organs, either as single agents or in combination with other immunosuppressants, many are also useful for treating inflammatory and autoimmune diseases, delayed hypersensitivity, graft versus host diseases and similar immune system associated diseases.

Currently used immunosuppressive drugs include antiproliferative agents, such as methotrexate, azathioprine, and cyclophosphamide. Since these drugs affect mitosis and cell division, they have severe toxic effects on normal cells with high turn-over rate such as bone marrow cells and the gastrointestinal tract lining. (Miller, *Semin. Vet. Med. Surg.* 12(3):144–149, 1997). Accordingly, marrow depression and liver damage are common side effects.

Antiinflammatory compounds used to induce immunosuppression include adrenal corticosteroids such as dexamethasone and prednisolone. The common side effects observed with the use of these compounds are frequent infections, abnormal metabolism, hypertension, and diabetes.

Other immunosuppressive compounds currently used to inhibit lymphocyte activation and subsequent proliferation include cyclosporine, FK506, and rapamycin. These drugs inhibit either the calcium dependent phosphatase calcineurin (cyclosporine and FK506) or inhibit the p70S6 kinase that is important for growth factor induced signaling (rapamycin). (Liu et al., *Cell* 66:807–815, 1991; Henderson et al., *Immun.* 73:316–321, 1991; Bierer et al., *Curr. Opin. Immun.* 5:763–773, 1993; Isoniemi (supra)). Cyclosporine and its relatives are among the most commonly used immunosuppressants. Cyclosporine is typically used for preventing or treating organ rejection in kidney, liver, heart, pancreas, bone-marrow, and heart-lung transplants, as well as for the treatment of autoimmune and inflammatory diseases such as Crohn's disease, aplastic anemia, multiple-sclerosis, myasthenia gravis, uveitis, biliary cirrhosis, etc. However, cyclosporines suffer from a small therapeutic dose window and severe toxic effects including nephrotoxicity, hepatotoxicity, hypertension, hirsutism, cancer, and neurotoxicity. (Philip and Gerson, *Clin. Lab. Med.* 18(4):755–765, 1998; Hojo et al., *Nature* 397:530–534, 1999).

Additionally, monoclonal antibodies, such as OKT3 have been used to prevent and/or treat graft rejection. Introduction of monoclonal antibodies into a patient, as with many biological materials, induces several side-effects, such as rigors and dyspnea. (Richards et al., *Cancer Res.* 59(9):2096–2101, 1999)

Within the context of many life-threatening diseases, organ transplantation is considered a standard treatment and, in many cases, the only alternative to death. The immune response to foreign cell surface antigens on the graft, encoded by the major histocompatibility complex (MHC) and present on all cells, generally precludes successful transplantation of tissues and organs unless the transplant tissues come from a compatible donor and the normal immune response is suppressed. Other than identical twins, the best compatibility and thus, long term rates of engraftment, are achieved using MHC identical sibling donors or MHC identical unrelated cadaver donors (Strom, *Clin. Asp. Autoimm.* 4:8–19, 1990). However, such ideal matches are difficult to achieve. Further, with the increasing need of donor organs an increasing shortage of transplanted organs currently exists. Accordingly, xenotransplantation has emerged as an area of intensive study, but faces many hurdles with regard to rejection within the recipient animal (Kaufman et al., *Annu. Rev. Immunol.* 13:339–367, 1995).

The host response to an organ allograft involves a complex series of cellular interactions among T and B lymphocytes as well as macrophages or dendritic cells that recognize and are activated by foreign antigen (Strom, supra; Cellular and Molecular Immunology, Abbas et al. (Eds.), WB Saunders Co., Penn., 1994). Co-stimulatory factors, primarily cytokines, and specific cell—cell interactions, provided by activated accessory cells such as macrophages or dendritic cells are essential for T-cell proliferation. These macrophages and dendritic cells either directly adhere to T-cells through specific adhesion proteins or secrete cytokines that stimulate T-cells, such as IL-12 and IL-15 (Strom, In: Organ Transplantation: Current Clinical and Immunological Concepts, 1989). Accessory cell-derived co-stimulatory signals stimulate activation of interleukin-2 (IL-2) gene transcription and expression of high affinity IL-2 receptors in T-cells (Pankewycz et al., *Transplantation* 47:318, 1989; Cantrell et al., *Science* 224:1312, 1991; Williams et al., *J. Immunol.* 132:2330–2337, 1984). IL-2, a 15 kDa protein, is secreted by T lymphocytes upon antigen stimulation and is required for normal immune responsiveness. IL-2 stimulates lymphoid cells to proliferate and differentiate by binding to IL-2 specific cell surface receptors (IL-2R). IL-2 also initiates helper T-cell activation of cytotoxic T-cells and stimulates secretion of interferon-γ (IFN-γ) which in turn activates cytodestructive properties of macrophages (Farrar et al., *J. Immunol.* 126:1120–1125, 1981). Furthermore, IFN-γ and IL-4 are also important activators of MHC class II expression in the transplanted organ, thereby further expanding the rejection cascade by enhancing the immunogenicity of the grafted organ (Pober et al., *J. Exp. Med.,* 157:1339, 1983; Kelley et al., *J. Immunol.,* 132:240–245, 1984).

The current model of a T-cell mediated response suggests that T-cells are primed in the T-cell zone of secondary lymphoid organs, primarily by dendritic cells. The initial interaction requires cell to cell contact between antigen-loaded MHC molecules on antigen-presenting cells (APCs) and the T-cell receptor (TCR)/CD3 complex on T-cells. Engagement of the TCR/CD3 complex induces CD154 expression predominantly on CD4 T-cells that in turn activate the APC through CD40 engagement, leading to improved antigen presentation (Grewal et al., *Ann. Rev Immunol.* 16:111–135, 1998). This is caused partly by upregulation of CD80 and CD86 expression on the APC, both of which are ligands for the important CD28 costimulatory molecule on T-cells. However, engagement of CD40 also leads to prolonged surface expression of MHC-antigen complexes, expression of ligands for 4-1BB and OX-40 (potent costimulatory molecules expressed on activated T-cells). Furthermore, CD40 engagement leads to secretion of various cytokines (e.g., IL-12, IL-15, TNF-α, IL-1, IL-6, and IL-8) and chemokines (e.g., Rantes, MIP-1α, and MCP-1), all of which have important effects on both APC and T-cell activation and maturation (Mackey et al., *J. Leukoc. Biol.* 63:418–428, 1998).

Similar mechanisms are involved in the development of autoimmune disease, such as type I diabetes. In humans and non-obese diabetic mice (NOD), insulin-dependent diabetes mellitus (IDDM) results from a spontaneous T-cell dependent autoimmune destruction of insulin-producing pancreatic β cells that intensifies with age. The process is preceded by infiltration of the islets with mononuclear cells (insulitis), primarily composed of T lymphocytes (Bottazzo et al., *J. Engl. J. Med.,* 113:353, 1985; Miyazaki et al., *Clin. Exp. Immunol.,* 60:622, 1985). A delicate balance between auto-aggressive T-cells and suppressor-type immune phenomena determine whether expression of autoimmunity is limited to insulitis or progresses to IDDM. In NOD mice, a model of human IDDM, therapeutic strategies that target T-cells have been successful in preventing IDDM (Makino et al., *Exp. Anim.,* 29:1, 1980). These include neonatal thymectomy, administration of cyclosporine, and infusion of anti-pan T-cell, anti-CD4, or anti-CD25 (IL-2R) monoclonal antibodies (mAbs) (Tarui et al., Insulitis and Type I Diabetes. Lessons from the NOD Mouse, Academic Press, Tokyo, p.143, 1986). Other models include those typically utilized for autoimmune and inflammatory disease, such as multiple sclerosis (EAE model), rheumatoid arthritis, graft versus host disease, systemic lupus erythematosus (systemic autoimmunity—NZBxNZWF$_1$ model), and the like. (see, for example, Theofilopoulos and Dixon, *Adv. Immunol.* 37:269–389, 1985; Eisenberg et al., *J. Immunol.* 125:1032–1036, 1980; Bonneville et al., *Nature* 344:163–165, 1990; Dent et al., *Nature* 343:714–719, 1990; Todd et al., *Nature* 351:542–547, 1991; Watanabe et al., *Biochem Genet.* 29:325–335, 1991; Morris et al., *Clin. Immunol. Immunopathol.* 57:263–273, 1990; Takahashi et al., *Cell* 76:969–976, 1994; Current Protocols in Immunology, Richard Coico (Ed.), John Wiley & Sons, Inc., Chapter 15, 1998).

The aim of all rejection prevention and autoimmunity reversal strategies is to suppress the patient's immune reactivity to the antigenic tissue or agent, with a minimum of morbidity and mortality. Accordingly, a number of drugs are currently being used or investigated for their immunosuppressive properties. As discussed above, the most commonly used immunosuppressant is cyclosporine, but usage of cyclosporine has numerous side effects. Accordingly, in view of the relatively few choices for agents effective at immunosuppression with low toxicity profiles and manageable side effects, there exists a need in the art for identification of alternate immunosuppressive agents. The present invention meets this need and provides other related advantages.

SUMMARY OF THE INVENTION

In brief, the present invention is directed to depsipeptides and congeners thereof (also referred to herein as "compounds") which have activity as immunosuppressant agents. In one embodiment, this invention discloses a method for suppressing an immune response of an animal by administering to the animal an effective amount of a compound having the following structure (I):

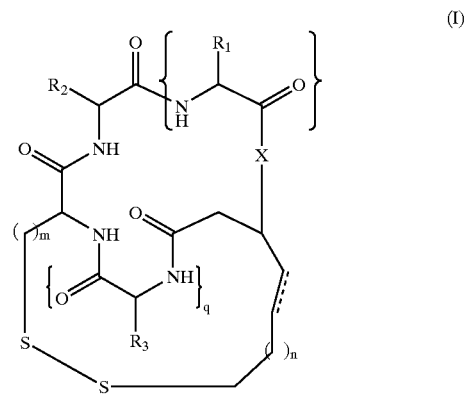

wherein m, n, p, q, X, Y, $R_1$, $R_2$ and $R_3$ are as defined below, including pharmaceutically acceptable salts and stereoisomers thereof.

In another embodiment, novel compounds are disclosed having structure (I) above, but excluding a specific known compound (i.e., FR901228). Further embodiments include compositions containing a compound of this invention in combination with a pharmaceutically acceptable carrier.

In practicing the methods of the present invention, the compounds may be administered to suppress the immune response in animals having autoimmune disease, inflammatory disease, or graft-versus-host disease, as well as to animals having undergone an allogeneic transplant or xenogeneic transplant. Further methods of this invention include administration of a compound of this invention for inhibiting the proliferation of lymphocytes, for enhancing graft survival following transplant by administration previous to, concurrently with, or subsequent to a transplant procedure (including allogeneic and xenogeneic transplant), for reducing IL-2 secretion from lymphocytes, for inhibiting induction of CD25 or CD154 on lymphocytes following stimulation, and/or for inducing anergy or apoptosis in activated T-cells while maintaining overall T-cell counts.

In another aspect the present invention provides methods for inducing immune system tolerance to an antigen by administering to an animal a dosage of a compound of structure (I). Also provided are methods for reducing secretion of TNF-α and for inhibiting the cell cycle of an activated T-cell prior to S-phase entry by administering to a compound of structure (I).

These and other aspects of this invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

Figure 1:
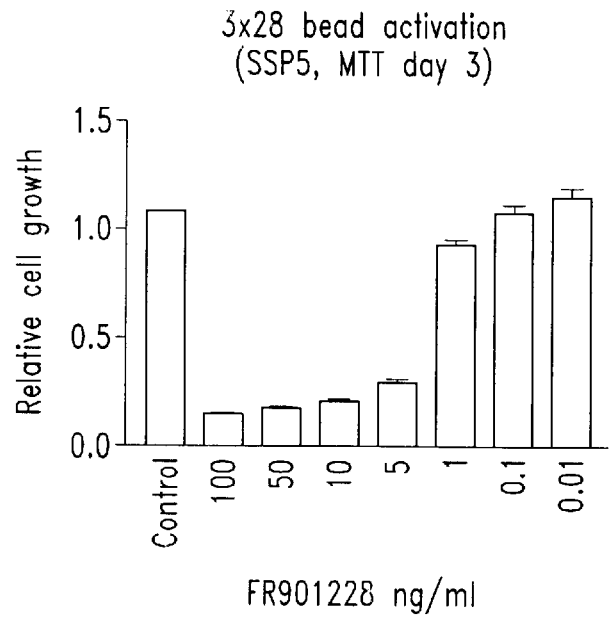
FIG. 1 is a bar graph representing dose dependent inhibition of peripheral blood lymphocyte (PBL) proliferation following incubation with FR901228 and stimulation by beads having anti-CD3 and anti-CD28 antibodies attached thereto.
Figure 2:
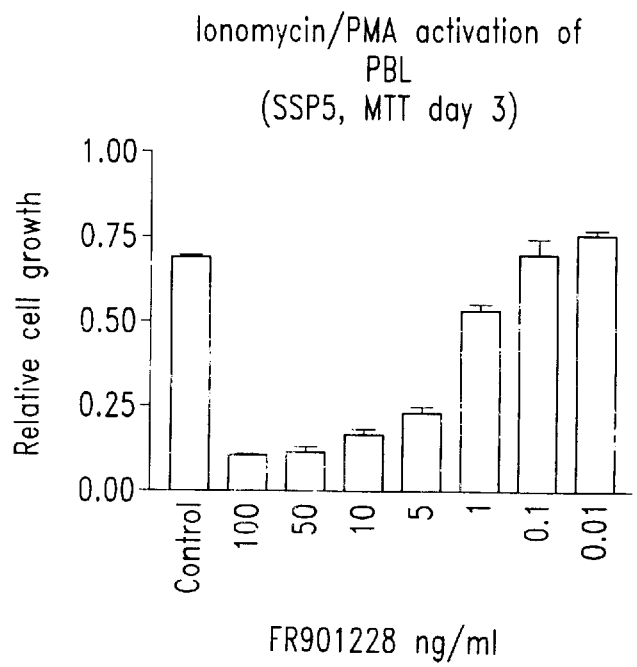
FIG. 2 is a bar graph depicting dose dependent inhibition of peripheral blood lymphocyte (PBL) proliferation, following incubation with FR901228 and stimulation with Ionomycin/PMA.
Figure 3:
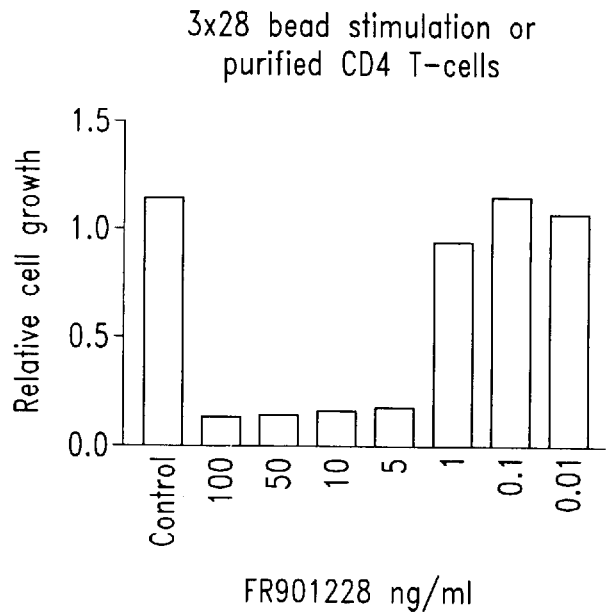
FIG. 3 is a bar graph depicting dose dependent inhibition of CD4 positive T-cell proliferation, following incubation with FR901228 and stimulation by beads having anti-CD3 and anti-CD28 antibodies attached thereto.
Figure 4:
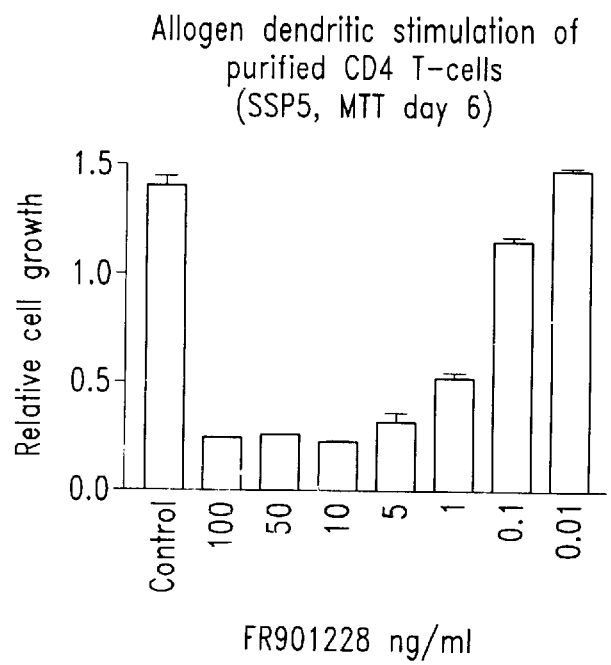
FIG. 4 is a bar graph depicting dose dependent inhibition of CD4 positive T-cell proliferation, following incubation with FR901228 and stimulation with in vitro generated allogenic dendritic cells.

As noted above, this invention is directed to compounds, specifically FR901228 and congeners thereof, that are useful in the context of immune suppression. FR901228 is a depsipeptide isolated from the terrestrial bacterium *Chromobacterium violaceum*. It was subsequently shown that FR901228 could inhibit transformation of Ha-ras transfected mouse fibroblasts (NIH-3T3). The mutant ras protein, in which valine replaces glycine-12, is capable of inducing morphological changes in NIH-3T3 cells. In these cells, the transformed phenotype is indicative of oncogenic activation and correlates with increased tumorigenicity. Recently, a large number of drug candidates as well as natural products have been identified that reverse this phenotype, and hence reverses transformation of tumorigenic cell lines. FR901228 is a natural product that has been identified in this effort, and has subsequently been shown to be highly active in animal-based models. As a result, FR901228 has received considerable attention as an antitumor agent.

More specifically, FR901228 is a bicyclic depsipetide (i.e., a peptide containing ester linkages as well as amide linkages) having the following structure:

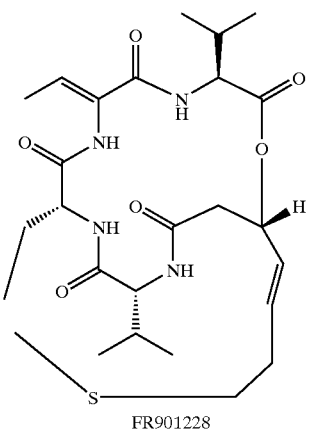

FR901228

While the molecular basis for activity of FR901228 is not known, it has been postulated that the disulfide bond may function as a redox-controlled conformational switch, and that the reducing environment inside a cell may convert this compound to the monocyclic di-thiol form (Khan et al., *J. Am. Chem. Soc.* 118:7237–7238, 1996).

Manufacture of FR901228 by a fermentation process is disclosed in U.S. Pat. No. 4,977,138 assigned to Fujisawa Pharmaceutical Co., Ltd. (hereby incorporated by reference in its entirety). In that patent, fermentation of a strain of bacterium belonging to the genus *Chromobacterium violaceum* WB968 is grown in a nutrient medium containing sources of assimilable carbon and nitrogen, and under aerobic conditions. Following completion of fermentation, FR901228 is recovered and purified by conventional techniques, such as by solvent extraction, chromatography or recrystallization.

In addition to isolation of FR901228 as a natural product, the total synthesis of this compound has now been reported by Khan et al. (supra). This procedure involves a 14-step process which provides FR901228 in 18% overall yield. In brief, the synthesis first involved the Carreira catalytic asymmetric aldol reaction to yield a thiol-containing β-hydroxy acid. The peptidic portion of the compound was assembled by standard peptide synthesis methods. The thiol-containing β-hydroxy acid was then coupled to the peptidic portion, and a monocyclic ring generated by formation of the ester (depsipeptide) linkage. The bicyclic ring system of FR901228 was then formed upon conversion of the protected thiols to a disulfide linkage.

In the practice of the present invention, FR901228 specifically, or compounds of structure (I) generally, have been discovered to have immunosuppressive properties. To this end, the compounds of the present invention include, in addition to FR901228, compounds having the following structure (I):

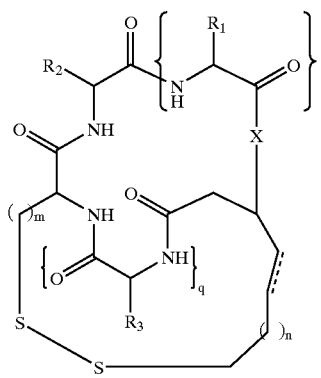

(I)

including pharmaceutically acceptable salts and stereoisomers thereof, wherein
m is 1, 2, 3 or 4;
n is 0, 1, 2 or 3;
p and q are independently 1 or 2;
X is O, NH or NR;
$R_1$, $R_2$ and $R_3$ are the same or different and independently an amino acid side-chain moiety or an amino acid side-chain derivative; and
R is a lower chain alkyl, aryl or arylalkyl moiety.

As used herein, the term "amino acid side-chain moiety" means any amino acid side-chain moiety present in naturally occurring proteins, including (but not limited to) the naturally occurring amino acid side-chain moieties identified in Table 1 below. Other naturally occurring side-chain moieties of this invention include (but are not limited to) the side-chain moieties of phenylglycine, 3,5-dibromotyrosine, 3,5-diiodotyrosine, hydroxylysine, naphthylalanine, thienylalanine, γ-carboxyglutamate, phosphotyrosine, phosphoserine and glycosylated amino acids such as glycosylated serine, asparagine and threonine.

TABLE 1

Representative Amino Acid Side Chain Moieties

| Amino Acid Side Chain Moiety | Amino Acid |
| --- | --- |
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_2$ | Lysine |
| —(CH$_2$)$_3$NHC(=NH)NH$_2$ | Arginine |
| —CH$_2$-(imidazole) | Histidine |
| —CH$_2$COOH | Aspartic acid |
| —CH$_2$CH$_2$COOH | Glutamic acid |
| —CH$_2$CONH$_2$ | Asparagine |
| —CH$_2$CH$_2$CONH$_2$ | Glutamine |

TABLE 1-continued

Representative Amino Acid Side Chain Moieties

| Amino Acid Side Chain Moiety | Amino Acid |
| --- | --- |
| —CH$_2$-(phenyl) | Phenylalanine |
| —CH$_2$-(phenyl)-OH | Tyrosine |
| —CH$_2$-(indole) | Tryptophan |
| —CH$_2$SH | Cysteine |
| —CH$_2$CH$_2$SCH$_3$ | Methionine |
| —CH$_2$OH | Serine |
| (pyrrolidinyl) | Proline |
| —CH(OH)CH$_3$ | Threonine |

When the amino acid side chain moiety is proline, it should be understood that the $R_1$, $R_2$ or $R_3$ group is joined to the adjacent nitrogen atom to form the pyrrolindinyl ring of proline. For example, in one embodiment of structure (I), wherein m, n, p and q are 1, the $R_1$ group may be proline—that is, $R_1$ taken together with the adjacent nitrogen atom forms a pyrrolindinyl ring as represented by the following structure (II):

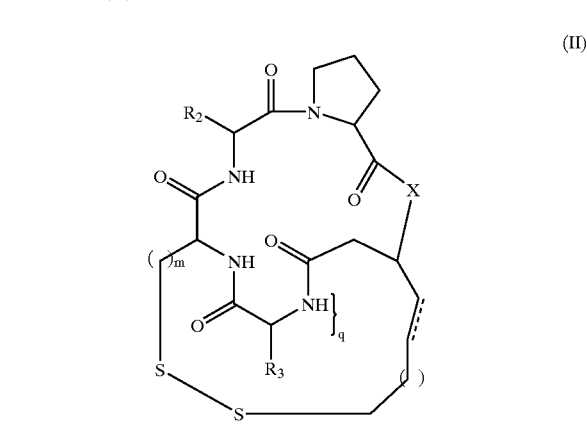

(II)

In addition to naturally occurring amino acid side-chain moieties, the amino acid side-chain moieties of the present invention also include various derivatives thereof. As used herein, an "amino acid side-chain moiety derivative" includes modifications and/or variations to naturally occurring amino acid side-chain moieties, and includes embodiments wherein $R_1$, $R_2$ and/or $R_3$ are joined to the bicyclic ring of structure (I) by a double or triple bond. For example, the amino acid side-chain moieties of alanine, valine, leucine, isoleucine, phenylglycine and phenylalanine may generally be classified as lower chain alkyl, aryl or aralkyl moieties. Derivatives of amino acid side-chain moieties include other straight chain or branched, cyclic or noncyclic, substituted or unsubstituted, saturated or unsaturated lower chain alkyl, aryl or aralkyl moieties.

As used herein, "lower chain alkyl moieties" contain from 1–12 carbon atoms, "lower chain aryl moieties" contain from 6–12 carbon atoms, and "lower chain aralkyl moieties" contain from 7–12 carbon atoms. Thus, in one embodiment, the amino acid side-chain derivative is selected from a $C_{1-12}$ alkyl, a $C_{6-12}$ aryl and a $C_{7-12}$ aralkyl, and in a more preferred embodiment, from a $C_{1-7}$ alkyl, a $C_{6-10}$ aryl and a $C_{7-11}$ aralkyl.

When $R_1$, $R_2$ and $R_3$ as set forth in structure (I) are attached by either a double or triple bond, a representative embodiment includes compounds of structure (III) wherein $R_2$ is joined by a double bond:

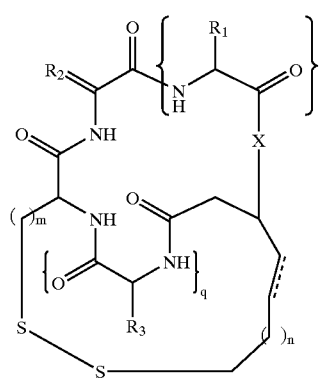

(III)

In one embodiment of structure (III), $R_2$ is an unsaturated lower chain alkyl, such as =$CHCH_3$, =$CHCH_2CH_3$ and the like. In the case of FR901288, $R_2$ of structure (III) is =$CHCH_3$, and m, n, p, q are each 1, X is oxygen, and the optional double bond is present (and in the trans-configuration).

Amino acid side-chain derivatives of this invention further include substituted derivatives of lower chain alkyl, aryl and aralkyl moieties, wherein the substituent is selected from (but are not limited to) one or more of the following chemical moieties: —OH, —OR, —COOH, —COOR, —CONH₂, —NH₂, —NHR, —NRR, —SH, —SR, —SO₂R, —SO₂H, —SOR, —PO₃R, —OPO₃R and halogen (including F, Cl, Br and I), wherein each occurrence of R is independently selected from a lower chain alkyl, aryl or aralkyl moiety. Moreover, cyclic lower chain alkyl, aryl and aralkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side-chain derivatives further include heteroalkyl derivatives of the alkyl portion of the lower chain alkyl and aralkyl moieties, including (but not limited to) alkyl and aralkyl phosphonates and silanes.

With regard p and q of structure (I), it should be understood that the size of the peptidic-portion of the ring may be increased by the addition of one (i.e., when either p or q is 2) or two (i.e., when both p and q are two) amino acids moieties. For example, when p is 2 and q is 1 (and X is oxygen), compounds of this invention include those of the following structures (IV):

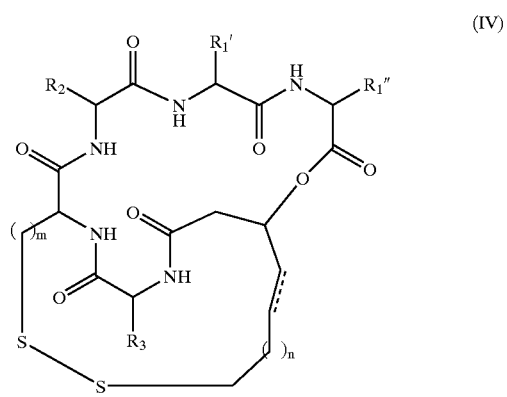

(IV)

In structure (IV) above, the amino acid side chain moiety corresponding to the $R_1$ group of structure (I) is designated $R_1'$ in the first instance and $R_1''$ in the second instance (since p is 2 in this embodiment) in order to clarify that these amino acid side chain moieties may be the same or different. In further embodiments, p is 1 and q is 2, or both p and q are 2.

In structure (I), the designation "===" represents an optional double bond. When present, the double bond may be in either the cis- or trans-configuration. In one embodiment, the double bond is in the trans-configuration, as it is in the case of FR901288.

Depending upon the choice of the X and Y moieties, compounds of the present invention include esters when X is oxygen, amides when X is NH or NR. For example, when both p and q are 1, representative compounds of this invention include esters and amides as represented by structures (VI) and (VII), respectively:

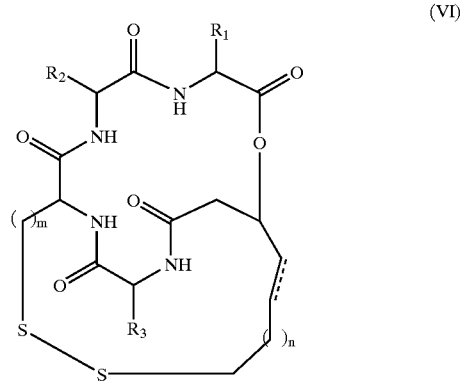

(VI)

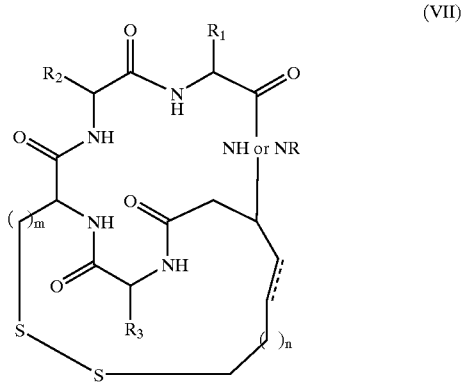

(VII)

The compounds of this invention may be prepared according to the following Reaction Scheme 1:

Reaction Scheme 1

Step (1):

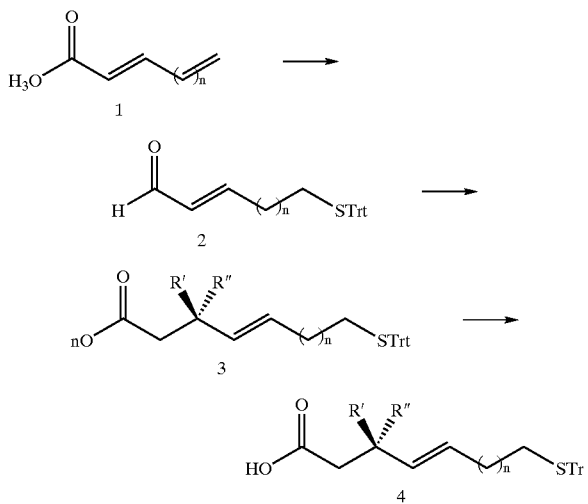

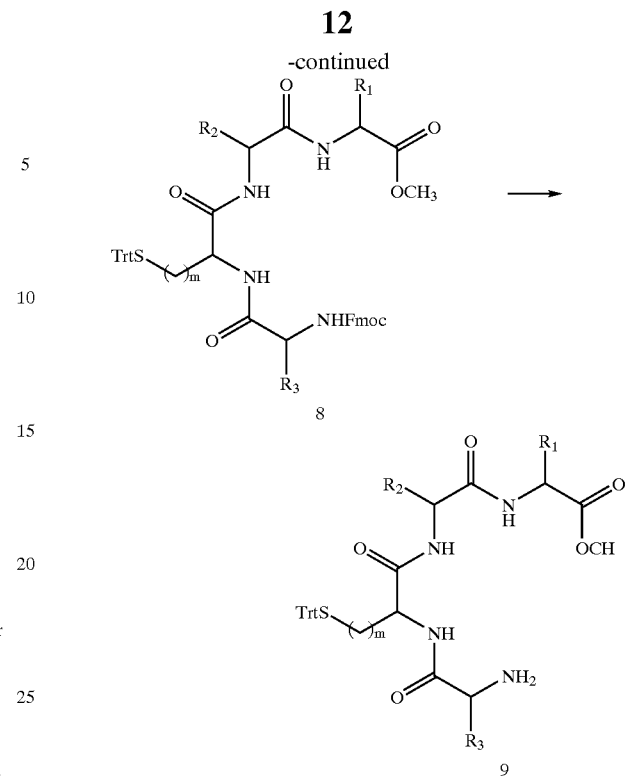

In step (1), aldehyde 2 is prepared from dienoate 1 (wherein n=1, 2 or 3) by the three-step procedure set forth by Kahn et al., *J. Am. Chem. Soc.* 118:7237–7238, 1996. Benzyl ester 3 is formed by Ti-(IV)-catalyzed addition of O-benzyl, O-TMS ketene acetal to aldehyde 2 (wherein R'=H and R"=OH, or R'=OH and R"=H). Hydrolysis of benzyl ester 3 with LiOH in MeOH/$H_2O$ gives hydroxy acid 4.

Step (2):

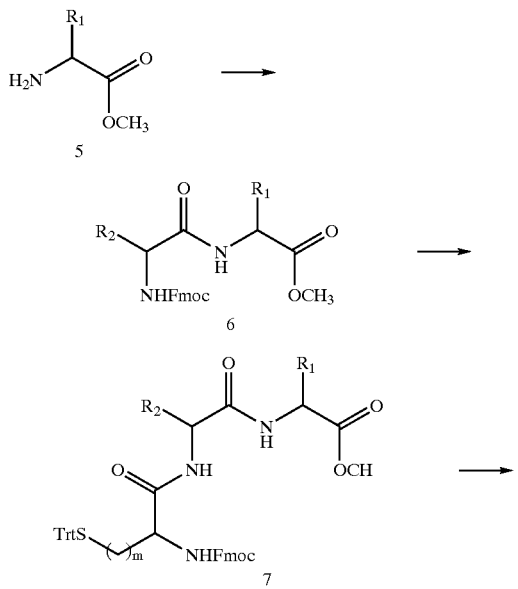

In step (2), the peptidic portion of the compound is prepared by standard peptide synthesis techniques starting with an appropriate amino acid methyl ester 5. Methyl ester 5 is reacted with an N-protected amino acid utilizing the BOP reagent to yield dipeptide 6, followed by coupling to N-Fmoc-cysteine-(S-triphenylmethyl) when m is 1, or an analog thereof when m is 2, to yield tripeptide 7. Tripeptide 7 is then converted to N-protected tetrapeptide 8, followed by deprotection of the FMOC group to yield tetrapeptide 9. In the above reaction scheme, $R_1$, $R_2$ and $R_3$ are the same or different and independently represent an amino acid side-chain moiety or derivative thereof as defined above. It will be recognized that the above technique corresponds to the synthesis of compounds of structure (I) when p and q are both 1. In embodiments wherein one or both of p and/or q are 2, the above technique is utilized to incorporate one or two additional amino acid groups into the peptidic portion of the compound.

Step (3)

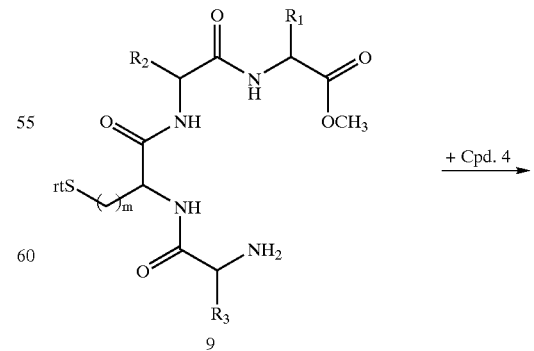

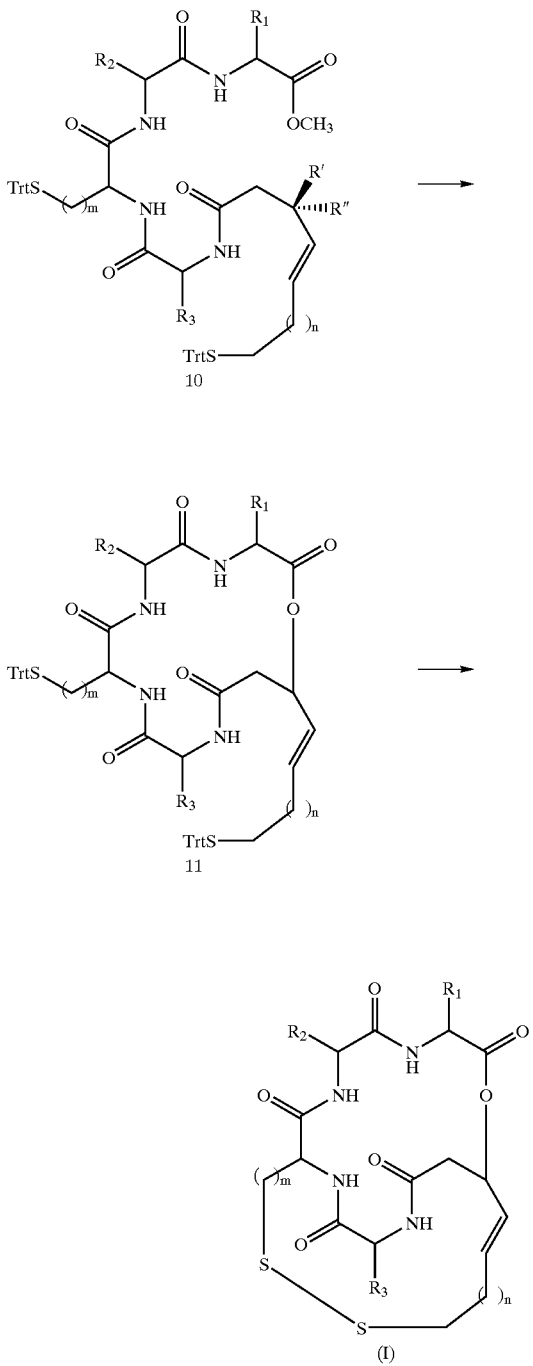

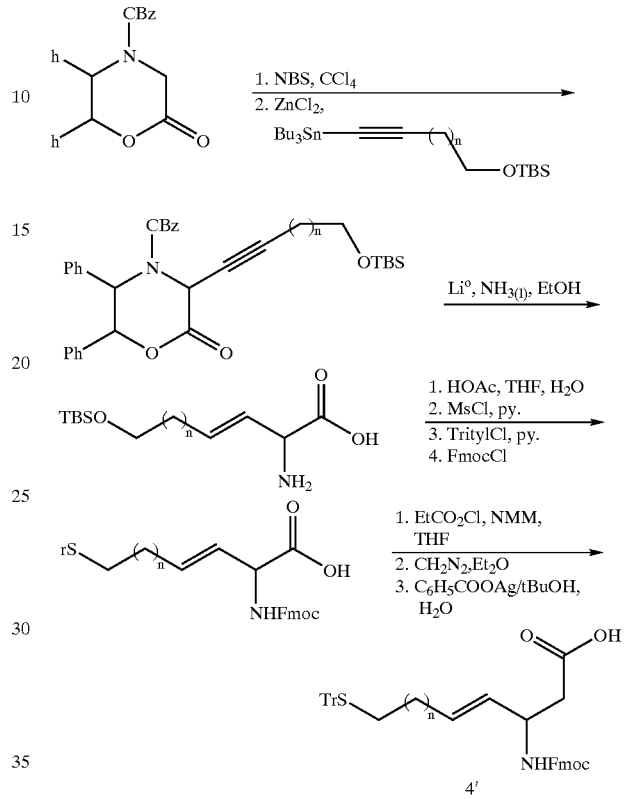

In step (3), coupling of tetrapeptide 9 and hydroxy acid 4 with BOP and DIEA yields the hydroxy methyl ester 10. LiOH-mediated hydrolysis of methyl ester 10 provides the corresponding carboxylic acid, which may then be converted to the monocyclic lactone intermediate 11 by cyclization with DEAD and PPh$_3$. Lastly, oxidation of the bis(S-triphenylmehtyl)lactone 11 with iodine in dilute MeOH solution provides compounds of the present invention having structure (I).

In this embodiment, compound 4' is made by the above procedures, and then added, in Step (3) above, to the peptidic portion made by Step (2). The resulting intermediate is cyclized as disclosed previously to yield compounds of structure (I).

In the case of X being NH or NR, such compounds may be made when R' or R" of compound 4 are NH or NHR, respectively. In addition, when the optional double bound of structure (I) is not present, the same reaction techniques may be employed, but utilizing the corresponding saturated intermediates.

The compounds of the present invention also include acid addition salts, which may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. As used herein, the term "pharmaceutically acceptable salt" of structure (I) is intended to encompass any and all suitable salt forms.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The present invention is related to the use of compounds of structure (I), in an animal subject, (preferentially a mammal and more preferably a human), for the treatment and/or prevention of immune response or immune-mediated responses and diseases, such as the prevention or treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; to treat or prevent graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treat infectious diseases causing abherent immune response and/or activation, such as traumatic or pathogen induced immune disregulation, including for example, that which are caused by hepatitis B and C infections, staphylococcus aureus infection, viral encephalitis, sepsis, parasitic diseases wherein damage is induced by an inflammatory response (e.g., leprosy); and to prevent or treat circulatory diseases, such as arteriosclerosis, atherosclerosis, vasculitis, polyarteritis nodosa and myocarditis. In addition the present invention may be used to prevent/suppress an immune response associated with a gene therapy treatment, such as the introduction of foreign genes into autologous cells and expression of the encoded product.

As used herein, "an immune response" refers to the body's reaction to foreign or self antigens so that they are neutralized and/or eliminated. Cell-mediated immune response involves the production of lymphocytes by the thymus (T-cells) in response to antigen exposure. This reaction is important in delayed hypersensitivity, rejection of tissue transplants and in some infections. In humoral immune response plasma lymphocytes (B cells) are produced in response to antigen exposure with subsequent antibody formation. This response can produce immunity or hypersensitivity. Nonspecific immune response, or inflammation is the response of the body's tissues and cells to injury from any source (e.g., trauma, organisms, chemical, ischemia, etc.). The initial response of the immune system to any threat involves vascular, chemical, and blood cell activities. Specific immune response is required when inflammation is inadequate to cope with injury or invasion by an organism or agent. It is directed and controlled by T and B cells. Cellular immunity refers to the T-cell response; humoral immunity is the term previously used to refer to B-cell responses. In addition, the reference herein to CD4 or CD8 cells or the like, is meant to infer that the cells are positive for the CD4 or CD8 cell surface marker.

Further uses may include the treatment and/or prophylaxis of: inflammatory and hyperproliferative skin diseases and cutaneous manifestations of immunologically mediated illnesses, such as, seborrhoeis dermatitis, angioedemas, erythemas, acne, and Alopecia areata; various eye diseases (autoimmune and otherwise); allergic reactions, such as pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis, and the like; inflammation of mucous and blood vessels; activity of certain viral infections, such as cytomegalovirus infection and Epstein-Barr virus infection.

In one embodiment, a method of treating a condition in an animal, the treatment of which is affected or facilitated by reduction of lymphocyte proliferation and/or activation (e.g., downregulation of CD25 and/or CD154), comprising the administration of an effective amount of a compound of structure (I) is provided. The method of treating a condition in an animal, the treatment of which is facilitated by inhibition of lymphocyte proliferation and/or inhibition of activation markers (e.g., CD25 and CD154), and inhibition of immune function, wherein the condition may be autoimmunity, inflammation, graft/tissue rejection, or includes any of a number of indications such as those herein described, that are immunologically induced or exacerbated is provided.

Accordingly, an embodiment of the invention is a method for the treatment of autoimmune diseases. While, another embodiment of the invention is a method for the prevention or treatment of rejection of foreign organ transplants comprising administering to a patient in need of such therapy a therapeutically effective amount of a compound of the present invention.

As noted above, cyclosporine is currently the leading drug used to prevent rejection of transplanted organs. The drug acts by inhibiting the function of calcineurin in lymphocytes, thereby preventing the body's immune system from mobilizing its vast arsenal of natural protecting agents to reject the transplant's foreign protein. Though cyclosporine is effective in fighting transplant rejection, it is nephrotoxic and is known to cause several undesirable side effects, including kidney failure, abnormal liver function, gastrointestinal discomfort, and induction of cancer. (Hojo et al., *Nature* 397:530–534, 1999)

Newer, safer drugs exhibiting fewer side effects are constantly being searched for in the field. The present invention provides for such immunosuppressive agents which, without wishing to be bound to a particular mechanism of action, appear to induce long lasting immune tolerance. FR901228 allows for partial activation of CD4 T-cells (e.g., induction of CD69, but reduction of CD25, CD137w, CD11a, CD134, CD54, CD95, and CD154 surface expression as well as reduction of IL-2 and/or TNF-α production).

CD4 T-cells activated in the presence of FR901228 do not undergo activation induced cell death (AICD), however they subsequently undergo apoptosis in vitro most likely due to the lack of IL-2 secretion and/or IL-2-receptor stimulation. Further, treatment of previously activated CD4 and CD8 T-cells with compounds of the class of FR901228, such as those depicted in structure (I), inhibits their growth and induces apoptosis within a short time, while leaving resting T-cells apparently unaffected. Induction of apoptosis in responding T-cells not only eliminates the activated T-cells, but also induces a state of long-term immune tolerance (Ferguson and Green, *Nature Med.* 5(11):1231–1232, 1999). The reason for this specific tolerance is not well understood. Nonetheless, immunization with non-dividing donor cells (e.g., dendritic cells or irradiated peripheral blood lymphocytes) in the presence of FR901228 prior to transplantation might very well confer specific tolerance to future host-versus-graft responses without further presence of FR901228.

The term "tolerance," as used herein, refers to a state of non-responsiveness of the immune system toward an antigen that it has the ability to react against. While not wishing to be bound to a particular mechanism, it is believed that tolerance is induced by the compounds of the present invention by the induction of apoptosis in activated T-cells. For example, if T-cells are activated by an antigen and subsequently undergo apoptosis, a subsequent immune response against this antigen will not occur. Tolerance induction by a particular compound may be tested by any methods and models known by those of skill in the art. In one example, primary and secondary stimulation by an antigen may be tested in the presence of the compounds of the present invention. In brief, an animal is inoculated with an antigen followed by a subsequent inoculation with the compound, about 2 weeks later the animal may be inoculated with the same antigen in the absence of the compound and secondary immune response measured. Accordingly, both primary and any secondary response may be measured by simple blood analysis. A sample that shows no secondary immune response demonstrates tolerance induced by the immunosuppressive compound. Further, standard in vitro assays can be utilized to determine T-cell activation, such as CTL assays or testing for IL-2 secretion.

In addition to induction of apoptosis CD4 and CD8 T-cells induced with a number of stimuli, including concurrent CD3 and CD28 engagement, Ionomycin/Phorbol myristic acid (PMA) stimulation, and allogeneic dendritic cell stimulation, demonstrate growth inhibition when treated with FR901228 either concurrently with stimulation or following stimulation. Accordingly, such compositions vastly improve upon drugs such as cyclosporine that inhibit CD4 T-cells very early in the activation cascade. This causes CD4 T-cells activated in the presence of cyclosporine to be defacto naïve or non-activated cells, which do not undergo apoptosis. Thus, when cyclosporine treatment is terminated the inhibited immune response will redevelop. In other words, if CD4 cells are in an active state in the presence of the of the compounds of the present invention these cells will undergo apoptosis and thus a lasting tolerance to the antigen, while when these same cells are treated with cyclosporine the immune response is only inhibited while cyclosporine remains present.

Further, FR901228 immune suppression leads to induction of anergy and/or apoptosis only in activated T-cells; thus, the general level of T-cells and other hematopoietic cells are maintained. In contrast, both cyclosporine and FK506 block the earliest events of T-cell activation, and thus prevent T-cells from entering a state at which they become susceptible to induction of apoptosis.

FR901228 has a number of features that aid its ability to act as a potent immunosuppressant. Accordingly, compounds of the class recited in structure (I) including FR901228 may have one or more of the following characteristics: inhibition of growth of CD4 and CD8 T-cells induced by CD3 and CD28 engagement, Ionomycin/PMA, or allogeneic dendritic cells; inhibition of ongoing growth of CD4 and/or CD8 T-cells when added after initial activation; inhibition of signal transduction pathways for both CD3/CD28 engagement and IL-2 stimulation; inhibition of the induction of CD25, CD134, CD137w, CD154, CD11a, CD54, and CD95 on CD4 T-cells; no significant affect on CD69 induction or activation induced downregulation of CD62L; reduction of IL-2 secretion from peripheral blood lymphocytes; reduction of TNF-α secretion from peripheral blood lymphocytes; inhibition of cell cycle prior to S-phase entry for activated T-cells; inhibition of p21cip/waf and C/EPB-α induction in activated T-cells; inhibition of c-myc expression in activated T-cells; inhibition of IL-2-induced proliferation of activated T-cells; and inhibition of CD154 at the transcriptional level. In addition, FR901228 does not affect bulk phosphorylation, as measured by phosphotyrosine Western blots. Thus, these observations indicate that compounds of structure (I) affect the T-cell activation pathway at multiple points, thus allowing activation to proceed into early stages, such as phosphorylation, but preventing subsequent events of activation and proliferation.

To determine whether a particular compound is an effective immunosuppressant, a variety of methodologies known in the art may be performed. In this regard, lymphocyte proliferation and/or activation may be measured following contact with the compound of interest prior to, simultaneous with, or subsequent to stimulation. For example, a key hallmark of T-cell activation and subsequent induction of proliferation (as well as being an initiator of inflammation) is the production of IL-2, IFN-γ, CD25, CD69, or CD154, which can be measured by a variety of methods, including ELISA and flow cytometry. Other experimental methods commonly employed to measure cell proliferation and cytokine secretion may also be utilized, including a colorimetric assay employing propidium iodide staining, MTT (3-[4,5-dimethylthiazole-2-yl], 2-5-diphenyltetrazolium bromide), vital stains, CFDA-SE (5-(and 6)-carboxyfluorescein diacetate-succinimidyl ester), cell count, bromodeoxyuridine incorporation, or a thymidine incorporation assay (see, e.g., Avian Dis. 43(2):172–181, 1999; Anticancer Res. 17(1B):725–728, 1997; Geller, Scand. J. Immunol. 35:327–334, 1992; Levine et al., Int. J Immun. 7(6):891–904, 1995; Hara et al., J. Exp. Med. 161:1513–1524, 1985; Harding et al., Nature 356:607–609, 1992; Linsley et al., Science 257:792–795, 1992; PCT Publication No. WO 95/33823).

Methods of activating lymphocytes and thus stimulating lymphocyte proliferation are well known in the art and include stimulation in the presence or absence of IL-2 with phytohemagglutinin (PHA), concanavalin A (ConA), anti-CD3 antibodies (in the presence or absence of anti-CD28 antibodies), allgeneic cells, superantigens or ionomycin/PMA. (Paul, Fundamental Immunology, Fourth Edition, Lippincott-Raven, 1998).

A variety of in vitro and animal models exist for testing and validating immunosuppressive compounds of the present invention and their applicability to a particular immune system related disease or indication. Accordingly, one of ordinary skill in the art could easily choose the appropriate model from those currently existing in the art. Such models include the use of NOD mice, where IDDM results from a spontaneous T-cell dependent autoimmune destruction of insulin-producing pancreatic β cells that intensifies with age (Bottazzo et al., J. Engl. J. Med., 113:353, 1985; Miyazaki et al., Clin. Exp. Immunol., 60:622, 1985). In NOD mice, a model of human IDDM, therapeutic strategies that target T-cells have been successful in preventing IDDM (Makino et al., Exp. Anim., 29:1, 1980). These include neonatal thymectomy, administration of cyclosporine, and infusion of anti-pan T-cell, anti-CD4, or anti-CD25 (IL-2R) monoclonal antibodies (mAbs) (Tarui et al., Insulitis and Type I Diabetes. Lessons from the NOD Mouse, Academic Press, Tokyo, p.143, 1986). Other models include, for example, those typically utilized for autoimmune and inflammatory disease, such as multiple sclerosis (EAE model), rheumatoid arthritis, graft-versus-host disease (transplantation models for studying graft rejection using skin graft, heart transplant, islet of Langerhans transplants, large and small intestine transplants, and the like), asthma models, systemic lupus erythematosus (systemic autoimmunity—NZBxNZWF$_1$ model), and the like. (see, for example, Takakura et al., *Exp. Hematol.* 27(12):1815–821, 1999; Hu et al., Immunology 98(3):379–385, 1999; Blyth et al., *Am J. Respir. Cell Mol. Biol.* 14(5):425–438, 1996; Theofilopoulos and Dixon, *Adv. Immunol.* 37:269–389, 1985; Eisenberg et al., *J. Immunol.* 125:1032–1036, 1980; Bonneville et al., *Nature* 344:163–165, 1990; Dent et al., *Nature* 343:714–719, 1990; Todd et al., *Nature* 351:542–547, 1991; Watanabe et al., Biochem Genet. 29:325–335, 1991; Morris et al., *Clin. Immunol. Immunopathol.* 57:263–273, 1990; Takahashi et al., *Cell* 76:969–976, 1994; Current Protocols in Immunology, Richard Coico (Ed.), John Wiley & Sons, Inc., Chapter 15, 1998).

Subjects in need of treatment to suppress the immune system include subjects with autoimmune disease; subjects undergoing transplantation; and subjects with cardiovascular disease; subjects with allergic reactions; and subjects with trauma or pathogenic induced immune disregulation. Examples of autoimmune diseases include insulin-dependent diabetes mellitus, asthma, psoriasis, ulcerative colitis, Crohn's disease, rheumatoid arthritis, multiple sclerosis, systemic lupus erythematosus, as well as others discussed above. Subjects with an organ or cell/tissue transplant are also in need of treatment to suppress the immune system in order to suppress or prevent organ transplant rejection. An "organ transplant" refers to transferring or "transplanting" an internal organ (e.g., heart, lung, kidney, liver, pancreas, stomach, large intestine and small intestine, and bone marrow) or external organ (e.g., skin) from a donor to a recipient, wherein the donor is genetically distinct from the individual or animal who has received the transplant. An "organ transplant" also includes cross-species transplants (i.e., xenotransplants).

"An effective amount" is the dosage of compound required to achieve the desired therapeutic and/or prophylactic effect; for example, the dosage of the compound which results in suppression of a naïve or memory immune response in the individual or animal, or which results in suppression of an organ transplant rejection in the subject. A "desired therapeutic effect and/or prophylactic effect" includes, for example, increasing the life span or ameliorating the symptoms of an individual or animal having or likely to have an autoimmune disease, such as asthma, psoriasis, ulcerative colitis, rheumatoid arthritis, multiple sclerosis, systemic lupus erythematosus, and the like. Examples of symptoms which can be ameliorated include: hyperglycemia in diabetes; joint pain; stiffness and immobility in rheumatoid arthritis; paralysis in multiple sclerosis; and rash and skin lesion in systemic lupus erythematosus. With respect to insulin-dependent diabetes mellitus, a "desired therapeutic or prophylactic effect" includes mitigating or preventing secondary complications resulting from the disease, such as vascular disorders. Suitable dosages will be dependent on the age, health and weight of the recipient, the extent of the disease, kind of concurrent treatment, if any, frequency of treatment and the nature of the effect desired. For example, dosages can be from about 0.001–100 milligrams per day. Ordinarily, from 0.1 to 50 milligrams per day in one or more applications is effective to obtain desired results. In certain embodiments, the dosage may be adjusted such that non-activated T-cells are maintained and substantially only activated T-cells are directed to apoptosis, anergy, and/or temporary functional non-responsiveness (i.e., the general level of T-cells and/or other dividing cells are maintained). In other embodiments, depsipeptide treatment achieves an immunosuppressive effect, while in other embodiments the dosage utilized does not affect hematopoietic cell division, and in yet other embodiments the dosage does not substantially affect cell division generally. However, effective dosage ranges can be readily determined during clinical trials and standard testing methodologies available in the art. These dosages are the effective amounts for the prevention or treatment of autoimmune diseases, the prevention or treatment of foreign transplant rejection and/or related afflictions, diseases and illnesses.

A "subject" is preferably a mammal, such as a human, but can also be an animal in need of veterinary treatment, e.g., domestic animals (e.g., dogs, cats, and the like), farm animals (e.g., cows, sheep, pigs, horses, chickens and the like) and laboratory animals (e.g., rats, mice, guinea pigs, and the like).

The compound can be administered alone or in conjunction with other pharmacologically active agents, e.g., together with other immunosuppressive agents or together with antibiotics and/or antiviral agents. Compounds that can be coadministered include steroids (e.g., methyl prednisolone acetate), NSAIDs and other known immunosuppressants, such as azathioprine, 15-deoxyspergualin, cyclosporine, mizoribine, mycophenolate mofetil, brequinar sodium, leflunomide, FK-506, rapamycin and related compounds. Dosages of these drugs will also vary depending upon the condition and individual to be treated.

An effective amount of the compound can be administered by an appropriate route in a single dose or in multiple doses.

Pharmaceutically acceptable salts include both the metallic (inorganic) salts and organic salts, a list of which is given in *Remington's Pharmaceutical Sciences,* 17th Edition, pg. 1418 (1985). It is well known to one skilled in the art that an appropriate salt form is chosen based on physical and chemical stability, flowability, hydroscopicity and solubility. As will be understood by those skilled in the art, pharmaceutically acceptable salts include, but are not limited to, salts of inorganic acids, such as hydrochloride, sulfate, phosphate, diphosphate, hydrobromide, and nitrate or salts of an organic acid, such as malate, maleate, fumarate, tartrate, succinate, citrate, acetate, lactate, methanesulfonate, p-toluenesulfonate or palmoate, salicylate and stearate. Similarly, pharmaceutically acceptable cations include, but are not limited to, sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are stereoisomers, crystal forms, hydrates and solvates of the compounds of the present invention.

As immunosuppressants, these compounds are useful in the treatment of autoimmune diseases, the prevention of rejection of foreign organ transplants and/or related afflictions, diseases and illnesses.

The compounds of this invention can be administered for the treatment of autoimmune diseases, the prevention of rejection of foreign organ transplants and/or related afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal or intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The active ingredient can be administered orally in solid dosage forms, such as capsules, tablets, troches, dragées, granules and powders, or in liquid dosage forms, such as elixirs, syrups, emulsions, dispersions and suspensions. (See, e.g., Chan et al., *Invest. New Drugs* 15:195–206, 1997, demonstrating the bioavailability of oral dosages of FR901228) The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an opthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents, such as sodium bisulfite, sodium sulfite, or ascorbic acid, either alone or combined, are suitable stabilizing agents. Also used are citric acid and its salts and sodium ethylenediaminetetraacetate (EDTA). In addition, parenteral solutions can contain preservatives, such as benzalkonium chloride, methyl- or propylparaben, and chlorobutanol. In certain embodiments, the composition is prepared by diluting 10 mg of lyophilized depsipeptide and 20 mg of povidone, USP with 2 ml of a solution containing 20% ethanol USP in propylene glycol, USP. The solution is then diluted further with 0.9% sodium chloride injection, USP to a final drug concentration in the range of 0.02 to 5.0 mg/ml.

For administration by inhalation, the compounds of the present invention may be conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery system for inhalation is a metered-dose inhalation (MDI) aerosol, which may be formulated as a suspension or solution of a compound of the present invention in suitable propellants, such as fluorocarbons or hydrocarbons.

For ocular administration, an opthalmic preparation may be formulated with an appropriate weight percent solution or suspension of the compounds of the present invention in an appropriate opthalmic vehicle, such that the compound is maintained in contact with the ocular surface for a sufficient time period to allow the compound to treat the mucosal surface or penetrate the corneal and internal regions of the eye.

The same dosage forms can generally be used when the compounds of this invention are administered stepwise or in conjunction with another therapeutic agent.

When drugs are administered in physical combination, the dosage form and administration route should be selected depending on the compatibility of the combined drugs. Thus, the term coadministration is understood to include the administration of the two agents concomitantly or sequentially, or alternatively as a fixed dose combination of the two active components.

From, the foregoing it will be appreciated that, although specific embodiments of the invention have been described herein for purposes of illustration, various modifications may be made without deviating from the spirit and scope of the invention. Accordingly, the invention is not limited except as by the appended claims. Further, all patents, patent applications, journal articles, and references referred to herein are incorporated by reference in their entirety.

EXAMPLES

Example I

Cell Growth and Preparation

Cells isolated from human blood are grown in X-vivo media (Biowhittaker Inc., Walkersville, Md.) and depending on use supplemented with or without 20 U/ml IL-2 (Boehringer Mannheim, Indianapolis, Ind.) and supplemented with 5% human serum (Biowhittaker), 2 mM Glutamine (Life Technologies, Rockville, Md.) and 20 mM HEPES (Life Technology). Jurkat E6-1 cells (ATCC, Manassas, Va.) are grown in RPMI 1640 (Life Technologies) supplemented with 10% fetal bovine serum (FBS) (Biowhittaker), 2 mM glutamine (Life Technologies), 2 mM penicillin (Life Technologies), and 2 mM streptomycin (Life Technologies).

Buffy coats from healthy human volunteer donors are obtained (American Red Cross, Portland, Oreg.). Peripheral blood mononuclear cells (PBMC) are obtained using Lymphocyte Separation Media (ICN Pharmaceuticals, Costa Mesa, Calif.) according to the manufacturers' instructions.

Peripheral blood lymphocytes (PBL) are obtained from the PBMC fraction by incubation in a culture flask (Costar, Pittsburgh, Pa.) or with uncoated Dynabeads (Dynal, Oslo, Norway), $1 \times 10^8$ cells/ml, 2 beads/cell, 2 h at 37° C. Monocytes and macrophages are removed by adherence to the culture flask or phagocytoze the paramagnetic beads that are depleted by magnetic cell separation according to the manufacture's instruction (Dynal). CD4 cells are purified from the PBL fraction by incubation with 10 $\mu$g/ml of monoclonal antibodies against CD8 (clone G10-1), CD20 (clone IF5), CD14 (clone F13) and CD16 (Coulter), $10^8$ cells/ml, 20 min at 4° C. After washing, cells are depleted twice with sheep anti-mouse Ig-coupled dynabeads ($10^6$ cells/ml, 6 beads/cell, 20 min at 4° C.) and magnetic cell separation. The purity of CD4 cells are routinely 91–95% as measured by flow cytometry.

Dendritic cells are generated from PBMC adhering to the culture flask (Costar), $10^8$ cells/ml, 2 h at 37° C. (without Dynabeads). After extensive washing, adherent cells are cultured for 7 days in media containing 500 U/ml GM-CSF (Boehringer-Mannheim) and 12.5 U/ml IL-4 (Boehringer-Mannheim). The resulting cell population is weakly adherent and expresses surface markers characteristic of dendritic cells (positive for HLA-DR, CD86, CD83, CD11c and negative for CD4). (note: all antibodies obtained from Becton Dickinson, Calif.).

The anti-CD3 mAb (OKT3) may be obtained from Ortho Biotec., (Raritan, N.J.) and the anti-CD28 mAb (9.3) may be obtained from Bristol-Myers Squibb, (Stamford, Conn.).

Example II

T-Cell Stimulation and Measurement of the Same

Figure 5A:
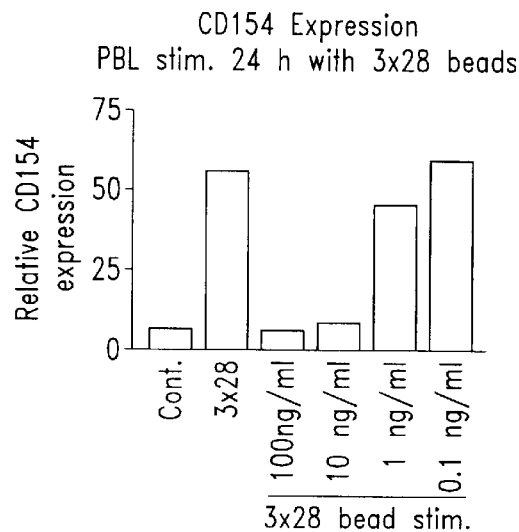
FIGS. 5A–5D are bar graphs depicting flow cytometry measurements of (A) CD154 expression, (B) CD25 expression, (C) CD69 expression, and (D) cell viability, following T-cell activation in the presence of varying levels of FR901228.
Figure 5B:
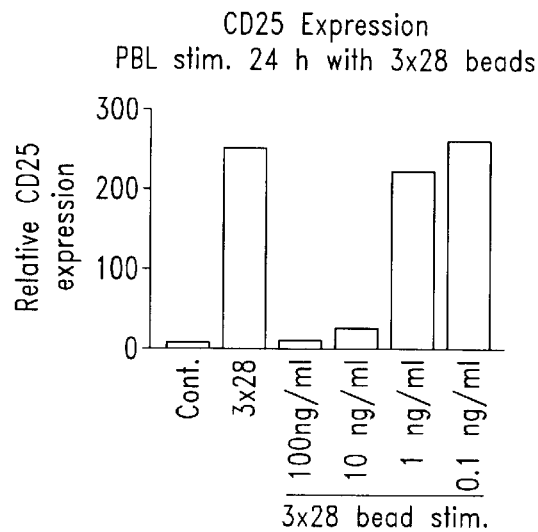
Figure 5C:
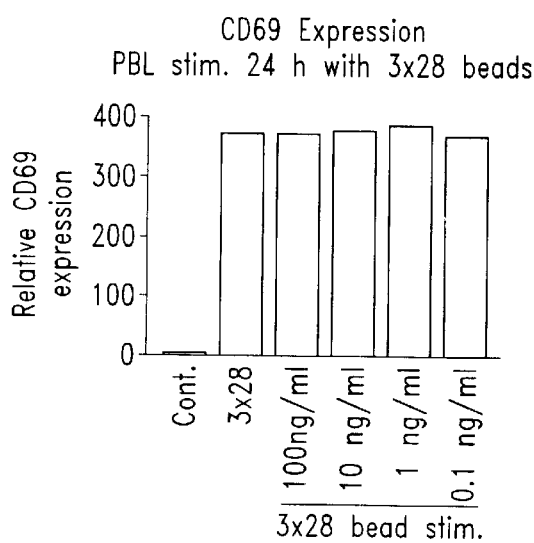
Figure 5D:
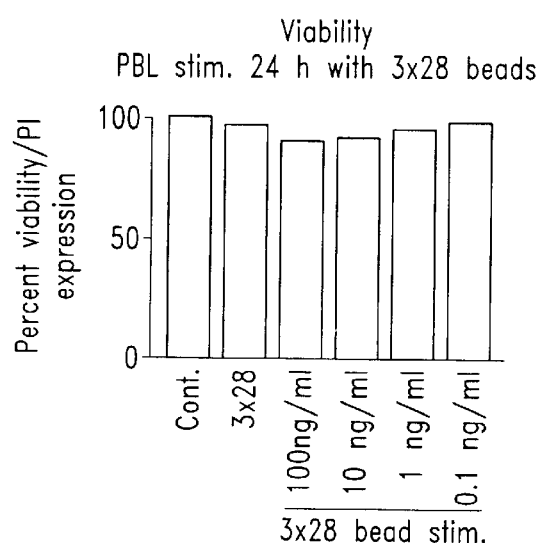

Cells are stimulated by three different methodologies 1) Dynabeads (M-450) covalently coupled to anti-CD3 (OKT-3) and anti-CD28 (9.3) antibodies (3×28 beads) according to the manufacturer's instructions (Dynal), 3 beads/cell, 2) Ionomycin (Calbiochem, La Jolla, Calif.) (100 ng/ml) and phorbol 12-myristate-13-acetate (PMA) (Calbiochem) (10 ng/ml), 3) allogeneic dendritic cells (25,000 dendritic cells/ 200,000 CD4 cells). All cells are stimulated at a concentration of $1 \times 10^6$ cells/ml. Cells are incubated with compounds of structure (I) (e.g., FR901228) (NCI, Bethesda, Md.) for 1 to 2 hours prior to stimulation as outlined above. Proliferation assays are conducted in quadruplicate in 96 well flat-bottom plates. Cells are stimulated at $1 \times 10^6$ cells/ml in a final volume of 200 µl. Proliferation is measured by MTT assay (MTT assay kit, Chemicon International Inc., Temecula, Calif.) at day 3 (stimulation method 1 and 2) or at day 6 (stimulation method 3), and results are presented as mean value of quadruplicates. PBL cultures or purified CD4 cell cultures are stimulated with 3×28 beads, ionomycin/ PMA or allogenic dendritic cells. As demonstrated in FIGS. 1–4 concentrations as low as 10 ng/ml of FR901228 completely inhibit proliferation of CD4 cells stimulated with 3×28 beads or ionomycin/PMA, whereas concentrations of 1 ng/ml of FR901228 or below have no significant effect (these experiments are performed by using a 2 hour incubation with FR901228 prior to stimulation). Interestingly, proliferation induced by allogenic dendritic cells is significantly inhibited by FR901228 at concentrations as low as 1 ng/ml. Further, greater cell survival is not affected by FR901228, as assessed by sub-G1 DNA measurement and integrity of the cell membrane (FIG. 5D). Lack of cytotoxicity of FR901228 is in agreement with results described by Byrd et al., *Blood* 94(4):1401–1408, 1999; Bates et al., Clinical Pharmacology, Programs and Proceedings of American Society of Clinical Oncology, Abstract 693, 1999; and Chassaing et al., *J. Chrmatogr. B* 719:169–176, 1998.

Growth and activation protocols are the same as those described above.

Example III

Activation Marker Assays

Figure 8A:
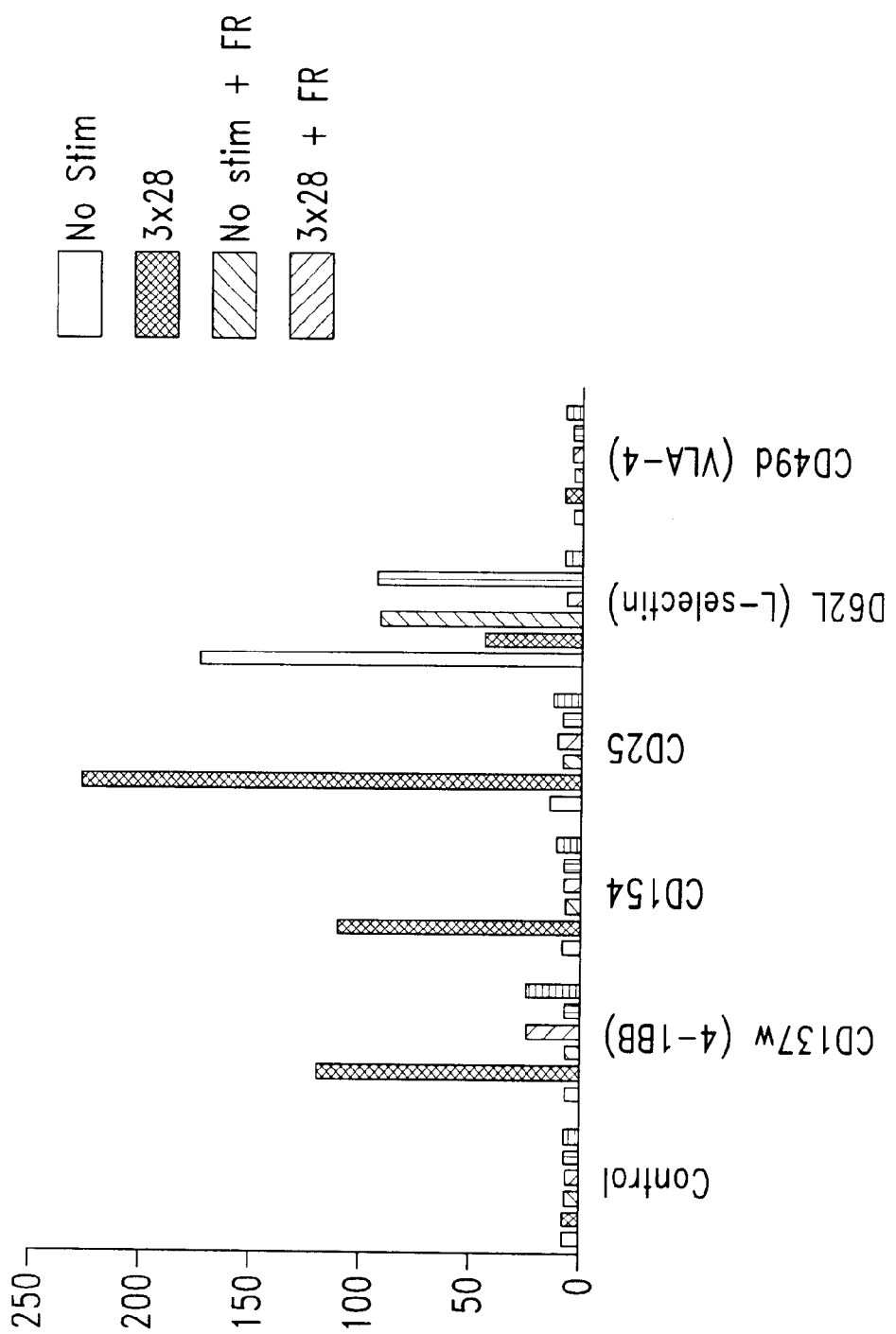
FIGS. 8A–8B are bar graphs depicting flow cytometry measurements of (A) CD137w, CD154, CD25, CD62L, and CD49d expression and (B) CD11a, CD134, CD26, CD54, CD95, and CD69 expression, following stimulation or no stimulation with 3×28 beads in the presence or absence of FR901228 (20 ng/ml).
Figure 8B:
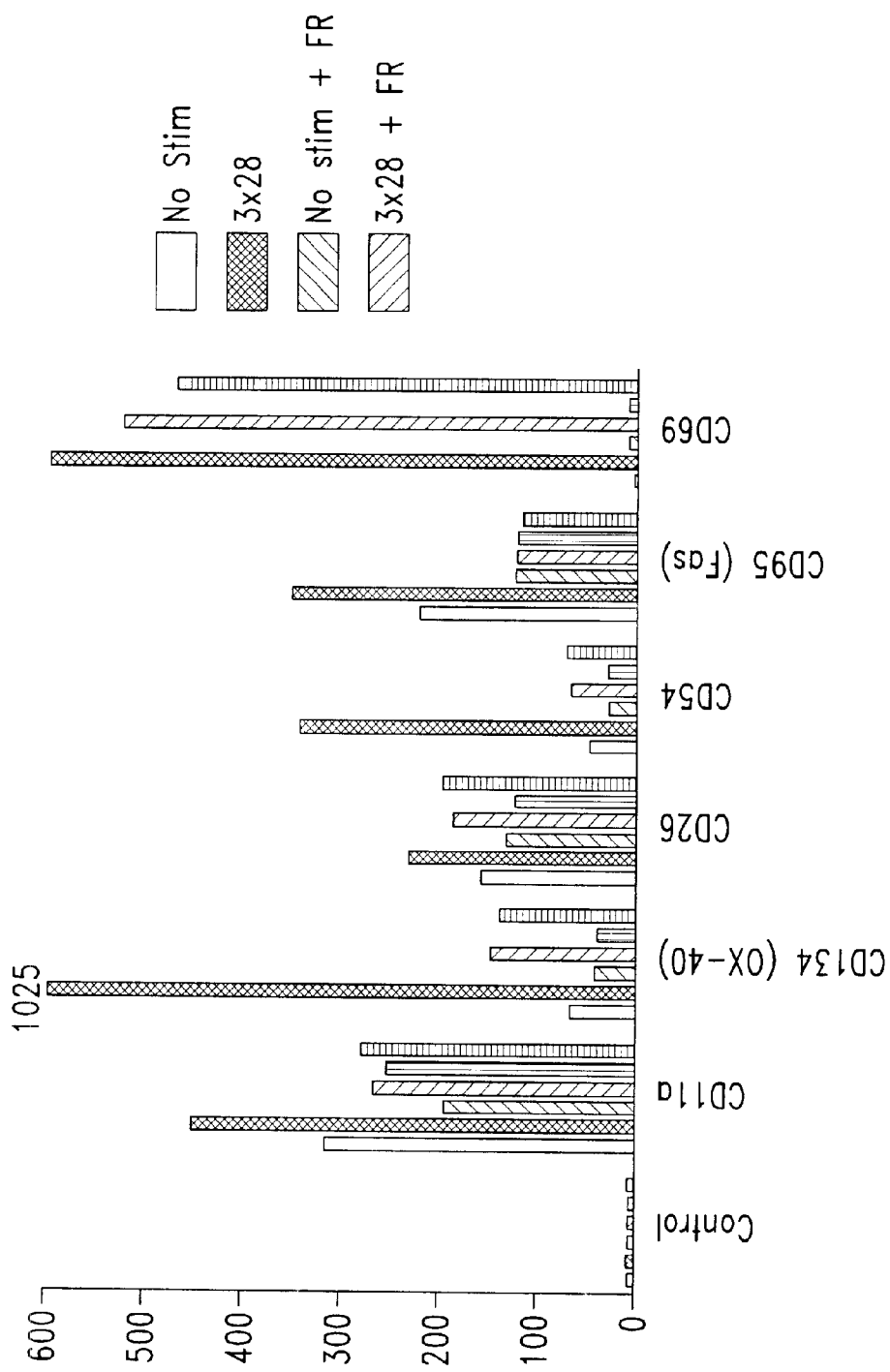

The effect of FR901228 on the induction of various activation markers on CD4 cells is studied. In this regard, cells are labeled with one or more of the following antibodies: anti-human CD4 Ab (Immunotech, Fullerton, Calif.), FITC-coupled anti-human CD11a Ab (Pharmingen), FITC-coupled anti-human CD26 Ab (Pharmingen), FITC-coupled anti-human CD49d Ab (Coulter), FITC-coupled anti-human CD54 Ab (Pharmingen and Becton Dickinson), FITC-coupled anti-human CD95 Ab (Pharmingen), FITC-coupled anti-human CD134 Ab (Pharmingen), FITC-coupled anti-human CD25 Ab (Becton Dickinson, Fullerton, Calif.), FITC-coupled anti-human CD69 Ab (Becton Dickinson), FITC- or PE-coupled anti-human CD154 Ab (Becton Dickinson), or FITC- or PE-coupled IgG1 isotype control Ab. Cells, $2 \times 10^5$ are labeled for 20 minutes at 4° C. with 2 µl of each antibody in a final volume of 30 µl, washed and resuspended in 1% parformaldehyde (Sigma, St. Louis, Mo.). Interestingly, CD25 and CD154 expression is strongly suppressed after 3×28 bead stimulation at concentrations as low as 10 ng/ml FR901228 (FIGS. 5A and 5B). In contrast, CD69 induction is not affected by 100 ng/ml FR901228 (FIG. 5C). In addition, FIGS. 8A–8B demonstrate inhibition of the induction of CD25, CD134, CD137w, CD154, CD11a, CD54, and CD95 on CD4 T-cells with no significant affect on CD69 induction or activation induced downregulation of CD62L (FIGS. 8A–8B). This suggests that FR901228 imposes a specific, however not complete, inhibition of proximal CD4 cell activation. Further, greater cell viability is not significantly affected by concentrations up to 100 ng/ml of FR901228 as measured by propidium iodide (PI) exclusion using standard flow cytometric procedures (see Dengler et al., *Anticancer Drugs.* 6(4):522–532, 1995).

FR901228 inhibition cannot be bypassed by ionomycin/ PMA activation, implying that FR901228 inhibition is downstream of the rise in intracellular calcium observed immediately after CD3 stimulation of CD4 cells.

Example IV

IL-2 and TNF-α Assays

Cells are prepared as described above. Supernatants from cells stimulated 24 h are subjected to an IL-2 or TNF-α enzyme linked immunosorbant assay (ELISA) according to the manufacturer's instructions (Biosource International, Sunnyvale, Calif.).

In an alternative assay, IL-2 is measured by intracellular staining of CD4 T-cells using flow cytometry. For intracellular labeling of IL-2 or IFN-γ, cells are first incubated with 1 µg/ml Monensin (Calbiochem) for 4 hours prior to assay. The cells are subsequently stained for surface proteins as described above, fixed and permeabilized using Becton Dickinson intracellular staining-kit, labeled with PE-coupled anti-human IL-2 Ab and FITC coupled anti-human IFN-γ or the corresponding control Abs as described by the manufacturer. Data acquisition and flow cytometric analysis is performed on a Becton Dickinson FACSCalibur flow cytometer using Cellquest software following the manufacturer's protocol (Becton Dickinson).

Figure 6:
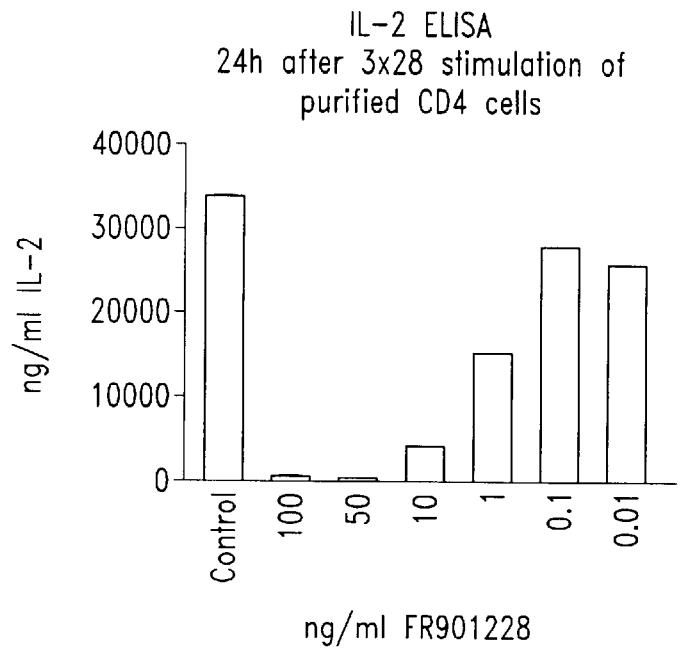
FIG. 6 is a bar graph depicting IL-2 expression as measured by ELISA 24 hours after 3×28 bead stimulation (anti-CD3 and anti-CD28 conjugated beads) of T-cells in the presence of varying levels of FR901228.

To study the mechanism behind FR901228 inhibition of CD4 cell proliferation, IL-2 and TNF-α production by activated CD4 cells was analyzed. FR901228 at concentrations as low as 10 ng/ml markedly inhibits IL-2 production measured by ELISA after 24 h of 3×28 (anti-CD3 and anti-CD28 antibody coupled beads) bead stimulation of purified CD4 cells (FIG. 6). A similar inhibition was observed using intracellular IL-2 measurement (not shown). However, diminished IL-2 production is not solely responsible for the lack of T-cell proliferation, as addition of 100 U/ml IL-2 (Boehringer Manheim) will not restore proliferation. The observation that FR901228 inhibits IL-2 production contrasts with previous results reported by Wang et al. who reported that FR901228 did not inhibit CD3-induced IL-2 production of the A1.1 T-cell hybridoma (*Oncogene* 17(12):1503–1508, 1998). The reason for this difference is currently unknown.

Figure 10A:
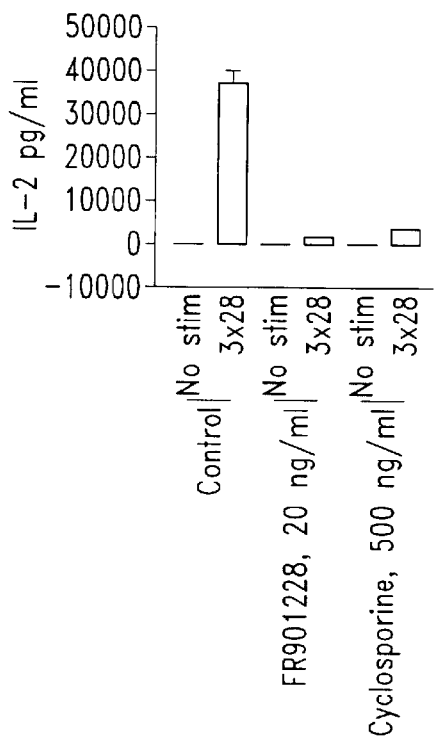
FIGS. 10A–10B are bar graphs depicting the presence of IL-2 and TNF-α in supematants of PBL cells following stimulation by 3×28 beads in the presence of FR901228 (20 ng/ml) and cyclosporine (500 ng/ml).
Figure 10B:
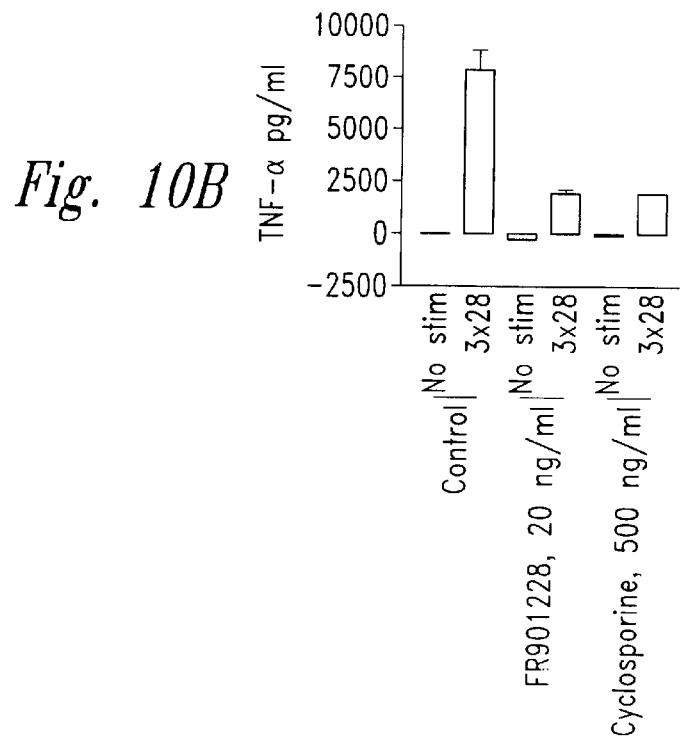

In further experiments, both IL-2 and TNF-α were measured by ELISA following 24 hours of stimulation of peripheral blood lymphocytes (PBL) with 3×28 beads in the presence or absence of 20 ng/ml of FR901228 and 500 ng/ml of cyclosporine (FIGS. 10A and 10B).

Example V

Proliferation Inhibition Assays

Figure 7:
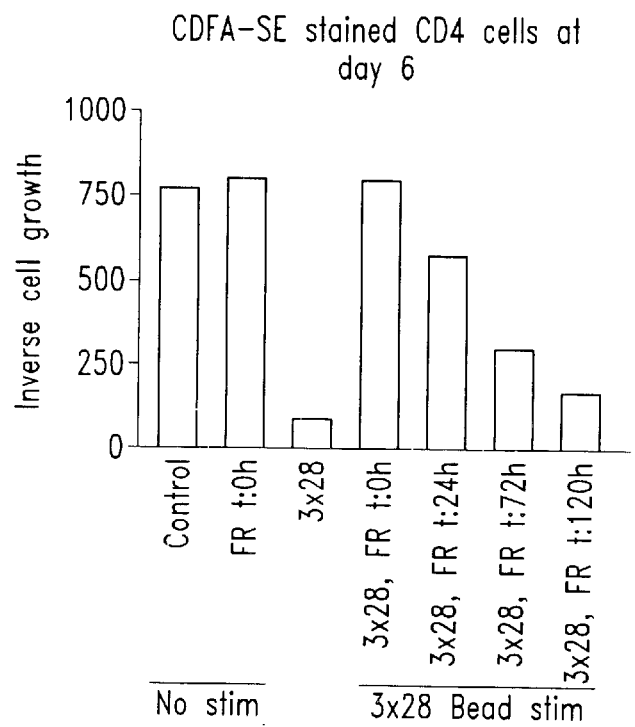
FIG. 7 is a bar graph depicting mean fluorescence intensity of CD4 cells stained with CFDA-SE at day 6 following 3×28 bead stimulation or no stimulation in combination with addition of FR901228 at varying time points.

Peripheral blood lymphocytes are prepared as described above, stimulated with 3×28 beads and stained with carboxyfluorescein diacetate succinimidyl ester (CFDA-SE) at day 6 post stimulation. Cell stimulation was carried out as indicated above and the cells were washed twice with PBS and resuspended in media and incubated with CFDA-SE (Molecular Probes, Oreg.). After about 10 minutes of staining, the cells are washed with media and FPS and dye incorporation was measured. FR901228 was added at various time points post-stimulation, at time 0 or at 24, 72, and 120 hours post-stimulation. FIG. 7 depicts flow data generated by CFDA-SE staining. The y-axis sets forth mean fluoresence intensity, which relates to the inverse of cell growth. Accordingly, the data indicates that cell growth of activated T-cells is inhibited by FR901228 either by contacting the cells with FR901228 prior to, concurrently with, or subsequent to stimulation with 3×28 beads.

Example VI

CD154 Expression on CD4 Cells

Figure 9:
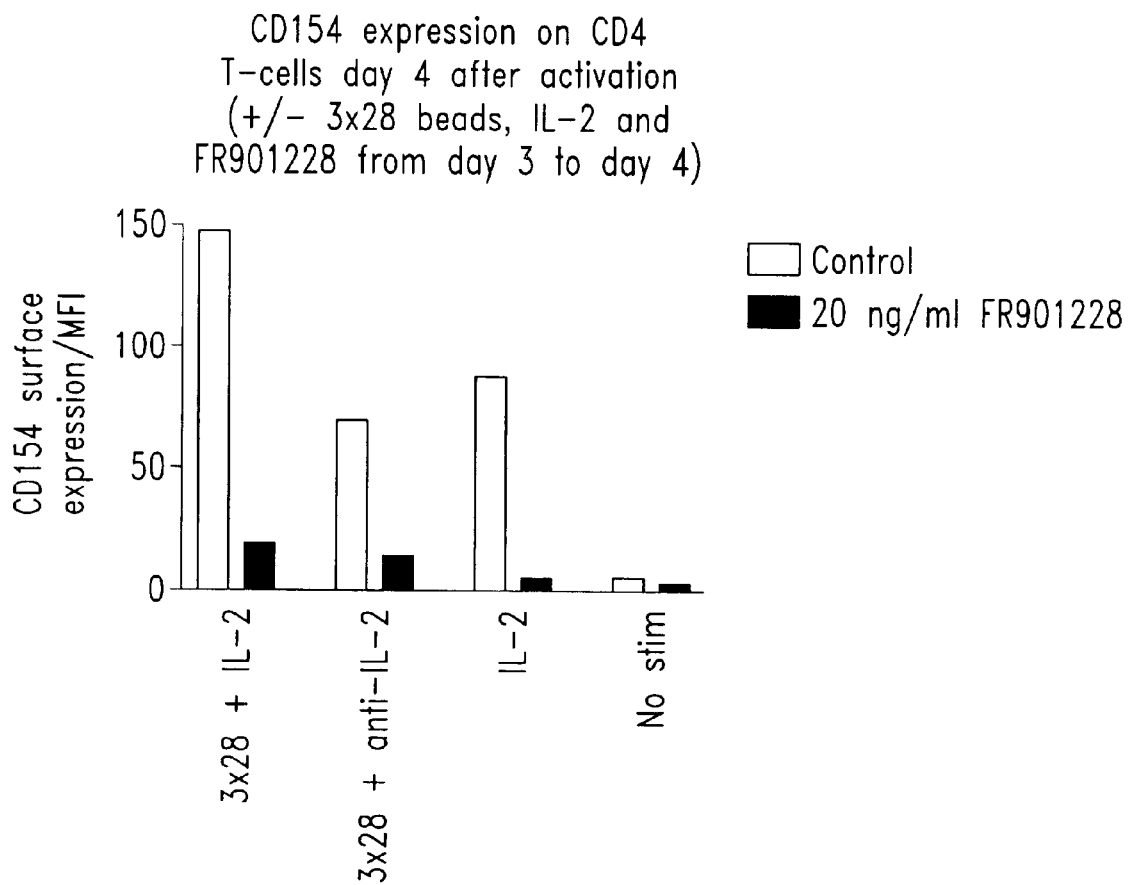
FIG. 9 is a bar graph depicting CD154 expression on CD4 cells following an initial stimulation with 3×28 beads in the presence of 20 units of IL-2 and a subsequent stimulation at day 3 to 4 with 3×28 beads, 20 units of IL-2, 3×28 beads w/20 units of IL-2, or no stimulation and 20 ng/ml of FR901228 (added on day three).

The effect of FR901228 on the induction of the CD154 activation marker on CD4 cells is studied. In this regard, cells are labeled with FITC-coupled anti-human CD4 Ab (Immunotech, Fullerton, Calif.), PE-coupled anti-human CD154 Ab (Becton Dickinson, Fullerton, Calif.), or FITC- or PE-coupled IgG1 isotype control Ab. Cells, 2×10$^5$ are labeled for 20 minutes at 4° C. with 2 μl of each antibody in a final volume of 30 μl, washed and resuspended in 1% parformaldehyde (Sigma, St. Louis, Mo.). The cells are stimulated for four days in the presence of 3×28 beads and/or 20 units/ml IL-2 or an anti-IL-2 antibody at day three, FR901228 is added to the culture at a concentration of 20 ng/ml. On day 4, mean fluorescence intensity is measured by flow cytometry. As depicted in FIG. 9, the presence of absence of IL-2 did not compensate for the suppression of CD154 expression induced by FR901228.

Example VII

Repression of CD154 at the Transcriptional Level

Figure 11:
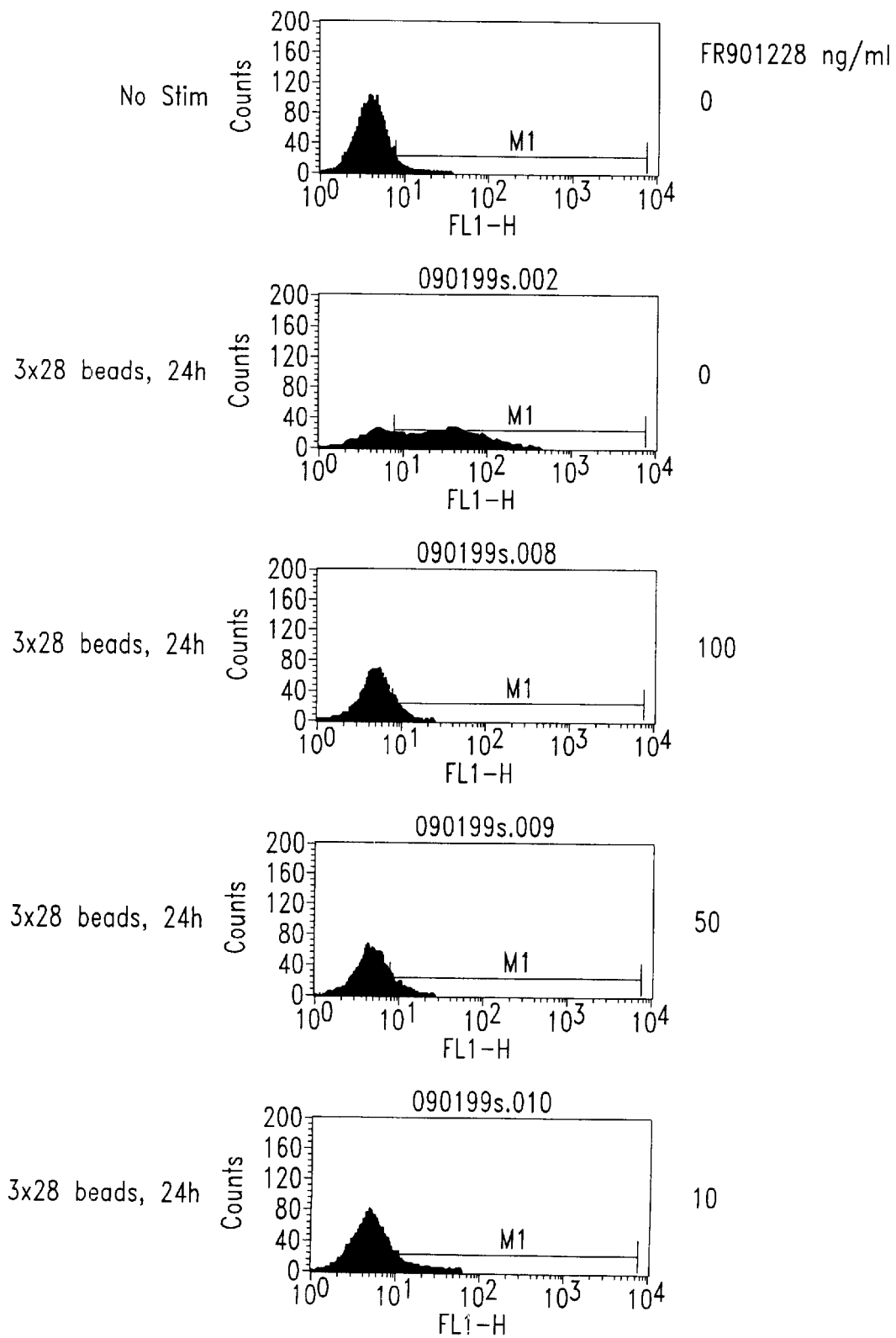
FIG. 11 depicts flow data of Jurkat T-cells stably transfected with a vector containing the nucleic acid sequence for green fluorescent protein under control of the CD154 promoter 24 hours following stimulation with 3×28 beads in the presence of 0, 10, 50, and 100 ng/ml of FR901228.

In this experiment Jurkat T-cells were stably transfected with a vector construct (p-EGFP1, Clonetech) wherein the nucleotide sequence encoding green fluorescent protein was operably linked to the CD154 promoter cloned from Jurkat cells. Following selection of cells containing the vector of interest, the cells were subjected to stimulation for 24 hours with 3×28 beads in the presence of varying concentrations (0 to 100 ng/ml) of FR901228. Fluorescence was then detected using flow cytometry. As is demonstrated by FIG. 11, only cells having 0 ng/ml of FR901228 showed induction of GFP expression beyond those cells having no stimulation.

In separate experiments, RT-PCR of the CD154 transcript was carried out after 18 hours of stimulation with 3×28 beads and various amounts of FR901228. These experiments demonstrated reduced levels of CD154 expression with increasing amounts of FR901228 (data not shown).

Experiments were also conducted using CD4 cells incubated with anti-sense constructs of c-myc. After stimulation by 3×28 beads for twenty-four hours, the anti-sense c-myc construct reduced CD154 expression as measured by flow cytometry by about 50% as compared to controls including: no construct, sense or transfection with a scrambled c-myc construct (data not shown). Accordingly, FR901228 and like compounds may target the activity of c-myc and its induction of CD154 as one mechanism of immune suppression.

Example VIII

Inhibition of Cell Cycle Prior to S-Phase Entry

Figure 12:
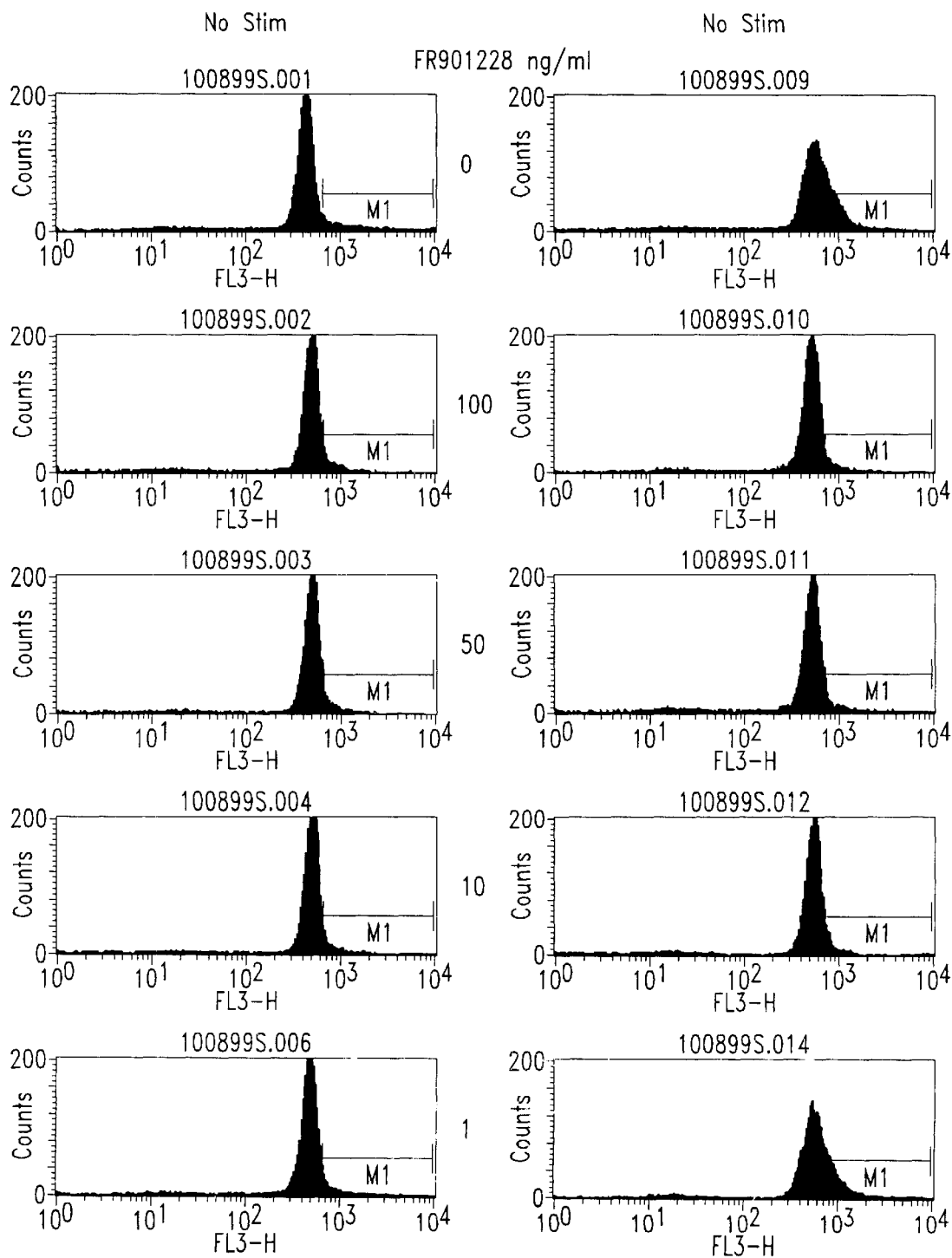
FIG. 12 depicts flow data of intracellular DNA staining of CD4 T-cells following no stimulation or stimulation with 3×28 beads for 24 hours, in the presence of 0, 1, 10, 50, and 100 ng/ml of FR901228.

Unstimulated and stimulated (3×28 bead stimulation) CD4 cells were incubated with varying concentrations FR901228 and the intracellular DNA content was measured by staining with propidium iodide (PI) using standard procedures. In brief, the cells were stained with a mixture of 1 μg/ml PI and 0.03% saponin in PBS for about 20 to 30 minutes. As indicated by FIG. 12, DNA synthesis does not take place in non-stimulated cells or in stimulated cells incubated with 10 to 100 ng/ml of FR901228. Accordingly, FR901228 appears to inhibit the cell cycle of activated T-cells prior to entry of S-phase.

Example IX

Radioisotope T-Cell Proliferation Assays

Peripheral blood mononuclear cells (PBMC) from healthy donors are separated by density centrifugation with ficoll-hypaque (LSM, Organon Teknika, Durham, N.C.). After washing, the PBMC with complete media (RPMI 1640 medium with 5% human serum, 100 mM glutamine, 1 mM sodium pyruvate, 0.1 mM non-essential amino acid, 2 mM Penicillin (Life Technologies), and 2 mM Streptomycin (Life Technologies), they are then irradiated at 7,500 RADS, and resuspended at 4–4.5×10$^6$ cells/ml in complete media. Another aliquot of PBMC are rosetted with neuraminidase-treated sheep red blood cells (SRBC). After another centrifugation with LSM, the SRBC of these rosetted T-cells are then lysed with ammonium chloride lysing buffer (Life Technologies). After washing twice with complete media, these purified T-cells are also resuspended at 2–2.5×10$^6$ cells/ml in complete media. The various dilutions of the test compound are added in triplicate at 50 μl/well into a 96-well flat-bottom microculture plate (Costar, Cambridge, Mass.). The T-cell suspension is then immediately distributed into the wells at 100 μl/well. After incubating the cells with the test compound for 30 min. at 37° C. in a humidified atmosphere of 5% $CO_2$-95% air, anti-CD3 Ab (OKT-3, Ortho Diagnostic, New Jersey) is added per well (final conc. of 10 ng/ml), followed by 50 μl of the irradiated PBMC. The culture plate is then incubated at 37° C. in a humidified atmosphere of 5% $CO_2$-95% air for 72 hours. The proliferation of T lymphocytes is assessed by measurement of tritiated ($^3$H) thymidine incorporation. During the last 18–24 hours of culture, the cells are pulse-labeled with 2 μCi/well of tritiated thymidine (NEN, Cambridge, Mass.). The cultures are harvested on glass fiber filters using a multiple sample harvester (MACH-II, Wallace, Gaithersburg, Md.). Radioactivity of filter discs corresponding to individual wells is measured by standard liquid scintillation counting methods (Betaplate Scint Counter, Wallace). Mean counts per minute of replicate wells are calculated and the results are expressed as concentration of compound required to inhibit tritiated thymidine incorporation of T-cells by 50%.

Example X

Prevention and/or Delay of Diabetes Onset in NOD or NODSCID Mice

This Example illustrates the ability of a representative depsipeptide compound FR901228 to prevent or delay diabetes onset in NOD and NODSCID mice.

FR901228 was dissolved in 10% DMSO in PBS and were administered i.p. to NOD or NODSCID mice every other day. Controls contained only the DMSO excipient (10% DMSO in PBS). Given that, NODSCID mice do not spontaneously develop diabetes, $30 \times 10^6$ NOD spleen cells from a 10 week old NOD mouse were injected into each NOD-SCID mouse (i.v.) at 4 weeks of age to induce diabetes. 0.5 mg/kg of FR901228 was administered at each treatment to twenty animals (ten NOD animals and ten NODSCID animals). Every two weeks the number of mice in each treatment group that had become diabetic was evaluated by measuring blood glucose levels using a glucometer at bi-weekly intervals. A reading of more than 200 mg/dl of blood glucose on two consecutive observations was considered indicative of frank diabetes. Average glucose numbers for these groups are presented in Table 2 below.

As shown in Table 2, in NODSCID mice, onset of frank diabetes was delayed by at least two weeks in those mice treated with the compound when compared to those mice that were treated with excipient only. Surprisingly, the results of the NOD mice were even more dramatic, in that no NOD mouse treated with the compound developed frank diabetes during the 18 week study, while 8 of 10 excipient treated mice developed frank diabetes in the same timeframe. Clearly, this data demonstrates an immunosuppressive effect in the delay of phenotypical diabetes onset.

TABLE 2A

FR901228 injected NOD SCID mice versus injection with DMSO vehicle

| donor | | | | | recipient | | | | | | | | | | | | |
|---|---|---|---|---|---|---|---|---|---|---|---|---|---|---|---|---|---|
| | | | | | | | | | age (wks) @ | | 5/9 | 5/23 | 6/6 | 6/20 | 7/4 | 7/18 | 8/1 | 8/15 |
| age (wks.) | genot sex | injection date | Cage card | ID | genot | sex | origine | injection | DOB | 6 | 8 | 10 | 12 | 14 | 16 | 18 | 20 |
| 10 | NOD | 3/27/00 | 518374 | 2659 | NOD-SCID | F | BSLC | 4 | rec'd | — | — | 482 | High | 536 | Sac'd by B.S. | | |
| | | 30 × 10^6 NOD spleen cells FR901228 | | | | | | | | | | | | | | | |
| — | — | — | — | 2660 | — | — | — | — | 22-Mar @ 4-6 wks. | — | 547 | 526 | 566 | 402 | Sac'd by B.S. | | |
| — | — | — | — | 2661 | — | — | — | — | | — | — | 343 | 596 | Dead | | | |
| — | — | — | — | 2662 | — | — | — | — | | — | — | 317 | 568 | Dead | | | |
| — | — | — | — | 2663 | — | — | — | — | — | — | — | 299 | 539 | 494 | Sac'd by B.S. | | |
| — | — | — | 518375 | 2654 | — | — | — | — | — | — | — | 412 | 338 | Dead | | | |
| — | — | — | — | 2655 | — | — | — | — | — | — | — | 441 | 240 | Dead | | | |
| — | — | — | — | 2656 | — | — | — | — | — | — | 261 | 527 | 494 | Dead | | | |
| — | — | — | — | 2657 | — | — | — | — | — | — | — | — | 399 | High | Dead | | |
| — | — | — | — | 2658 | — | — | — | — | — | — | — | — | 285 | 576 | 558 | 571 | Dead |
| 10 | NOD | 3/27/00 | 518376 | 2675 | NOD-SCID | F | BLSC | 4 | rec'd | 383 | Dead | 5/25 | | | | | |
| | | 30 × 10^6 NOD spleen cells (DMSO Vehicle only) | | | | | | | | | | | | | | | |
| — | — | — | — | 2676 | — | — | — | — | 22-Mar @ 4-6 wks. | — | 439 | 428 | Dead | 6/13 | | | |
| — | — | — | — | 2677 | — | — | — | — | | — | 254 | 377 | High | 337 | Sac'd 7/12 by B.S. | | |
| — | — | — | — | 2678 | — | — | — | — | | — | 223 | 448 | High | 523 | Sac'd 7/12 by B.S. | | |
| — | — | — | — | 2679 | — | — | — | — | — | 287 | High | High | Dead | 6/8 | | | |
| — | — | — | 518377 | 2381 | — | — | — | — | — | — | — | 311 | Sac'd by B.S. | | | | |
| — | — | — | — | 2382 | — | — | — | — | — | — | — | 447 | 516 | Sac'd by B.S. | | | |
| — | — | — | — | 2383 | — | — | — | — | — | — | — | 324 | 405 | Sac'd by B.S. | | | |
| — | — | — | — | 2384 | — | — | — | — | — | — | — | — | 456 | Sac'd by B.S. | | | |
| — | — | — | — | 2385 | — | — | — | — | — | — | — | 423 | 463 | Sac'd by B.S. | | | |

TABLE 2B

FR901228 injected NOD mice versus injection with DMSO vehicle

| | | | | recipient | | | 5/9 | 5/23 | 6/6 | 6/20 | 7/4 | 7/18 | 8/1 | 8/15 |
|---|---|---|---|---|---|---|---|---|---|---|---|---|---|---|
| | | | | | age (wks) @ | | | | | wks. Post transfer | | | | |
| | Cage card | ID | genot. | sex | origine | injection | DOB | 6 | 8 | 10 | 12 | 14 | 16 | 18 | 20 |
| FR901228 Treated | 518450 | 2664 | NOD | F | BSLC | N/A | rec'd | — | — | — | — | — | — | — |
| | | 2665 | — | — | — | — | 23-Mar | — | — | — | — | — | — | — |
| | | 2666 | — | — | — | — | "@ 4 wks. | — | — | — | — | — | — | — |
| | | 2667 | — | — | — | — | — | | | | | | | |
| | | 2668 | — | — | — | — | — | | | | | | | |
| | 518449 | 2669 | — | — | — | — | — | | | | | | | |
| | | 2670 | — | — | — | — | — | | | | | | | |
| | | 2671 | — | — | — | — | — | | | | | | | |
| | | 2672 | — | — | — | — | — | | | | | | | |
| | | 2674 | — | — | — | — | — | | | | | | | |
| Controls with 10% DMSO Vehicle | 518448 | 2386 | NOD | F | BSLC | N/A | rec'd | — | — | — | — | 238 | 423 | 452 |
| | | 2387 | — | — | — | — | 23-Mar @ 4 wks. | — | — | — | — | — | — | — |
| | | 2388 | — | — | — | — | | — | 302 | 513 | Sac'd by B.S. | | | |
| | | 2389 | — | — | — | — | | — | — | — | — | — | 310 | |
| | | 2390 | — | — | — | — | | — | — | — | 545 | 554 | Sac'd 7/12 by B.S. | |
| | 518451 | 2391 | — | — | — | — | | — | — | — | — | — | — | — |
| | | 2392 | — | — | — | — | | — | — | — | — | 308 | 455 | 504 |
| | | 2393 | — | — | — | — | | — | — | — | — | — | — | 466 |
| | | 2394 | — | — | — | — | | — | 390 | 391 | Sac'd by B.S. | | | |
| | | 2395 | — | — | — | — | | — | — | — | — | 207 | 354 | 126 |

From the foregoing, it will be evident that although specific embodiments of the invention have been described herein for the purpose of illustrating the invention, various modifications may be made without deviating from the spirit and scope of the invention.

I claim:

1. A method for inhibiting the proliferation of CD4 T-Cells, comprising administering to an animal an effective amount of a compound having the following structure:

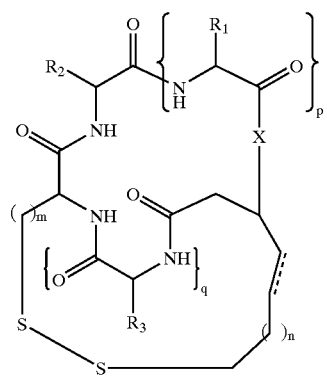

(I)

or a pharmaceutically acceptable salt or stereoisomer thereof,
wherein
m is 1, 2, 3 or 4;
n is 0, 1, 2 or 3;
p and q are independently 1 or 2;
X is O, NH or NR;
$R_1$, $R_2$ and $R_3$ are the same or different and independently an amino acid side-chain moiety or an amino acid side-chain derivative; and
R is a lower chain alkyl, aryl or arylalkyl moiety.

2. A method for inhibiting the proliferation of CD8 T-Cells, comprising administering to an animal an effective amount of a compound having the following structure:

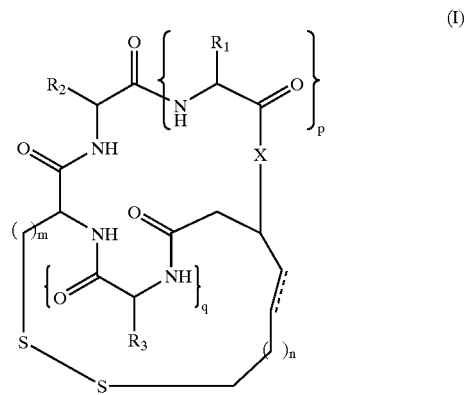

(I)

or a pharmaceutically acceptable salt or stereoisomer thereof,
wherein
m is 1, 2, 3, or 4;
n is 0, 1, 2, or 3;
p and q are independently 1 or 2;
X is O, NH or NR;
$R_1$, $R_2$ and $R_3$ are the same or different and independently an amino acid side-chain moiety or an amino acid side-chain derivative; and
R is a lower chain alkyl, aryl or arylalkyl moiety.

3. A method for treating an infectious disease, comprising administering to an animal an effective amount of a compound having the following structure:

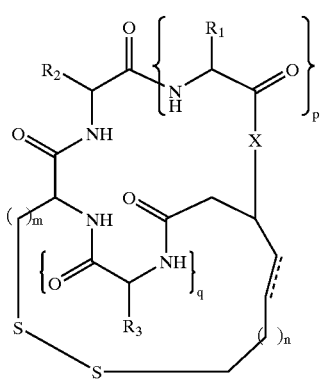

(I)

or a pharmaceutically acceptable salt or stereoisomer thereof, wherein
m is 1, 2, 3 or 4;
n is 0, 1, 2 or 3;
p and q are independently 1 or 2;
X is O, NH or NR;
$R_1$, $R_2$ and $R_3$ are the same or different and independently an amino acid side-chain moiety or an amino acid side-chain derivative; and
R is a lower chain alkyl, aryl or arylalkyl moiety.

4. A method for treating parasitic diseases wherein damage is induced by an inflammatory response, comprising administering to an animal an effective amount of a compound having the following structure:

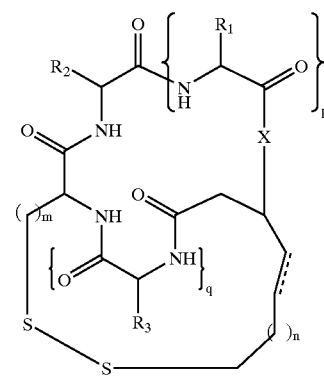

or a pharmaceutically acceptable salt or stereoisomer thereof, wherein
m is 1, 2, 3 or 4;
n is 0, 1, 2 or 3;
p and q are independently 1 or 2;
X is O, NH or NR;
$R_1$, $R_2$ and $R_3$ are the same or different and independently an amino acid side-chain moiety or an amino acid side-chain derivative; and
R is a lower chain alkyl, aryl or arylalkyl moiety.

5. A method for preventing or treating circulatory diseases, comprising administering to an animal an effective amount of a compound having the following structure:

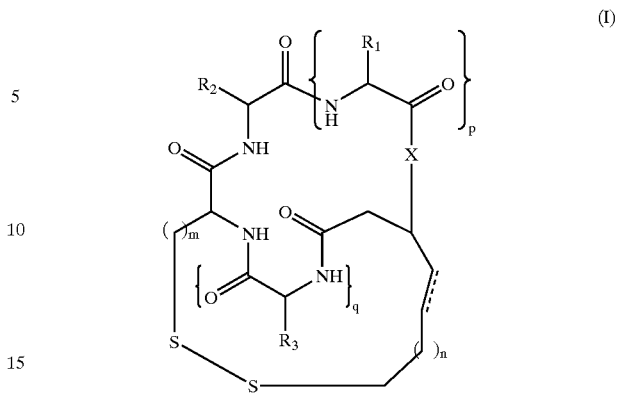

(I)

or a pharmaceutically acceptable salt or stereoisomer thereof, wherein
m is 1, 2, 3 or 4;
n is 0, 1, 2 or 3;
p and q are independently 1 or 2;
X is O, NH or NR;
$R_1$, $R_2$ and $R_3$ are the same or different and independently an amino acid side-chain moiety or an amino acid side-chain derivative; and
R is a lower chain alkyl, aryl or arylalkyl moiety.

6. The method of claim 5, wherein said circulatory disease is selected from the group consisting of arteriosclerosis, atherosclerosis, vasculitis, polyarteritis nodosa, and myocarditis.

7. A method of treating a condition in an animal, the treatment of which is affected or facilitated by reduction of lymphocyte proliferation and/or activation, comprising administering to an animal an effective amount of a compound having the following structure:

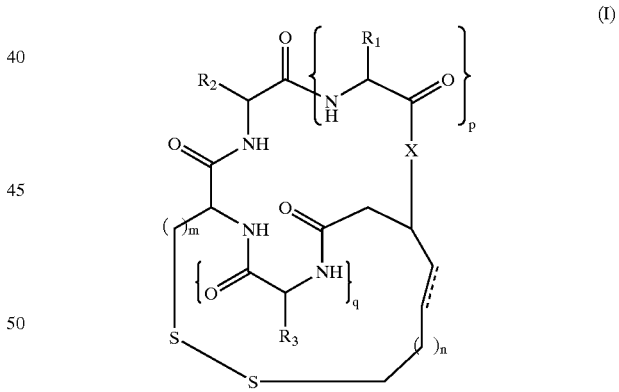

(I)

or a pharmaceutically acceptable salt or stereoisomer thereof, wherein
m is 1, 2, 3 or 4;
n is 0, 1, 2 or 3;
p and q are independently 1 or 2;
X is O, NH or NR;
$R_1$, $R_2$ and $R_3$ are the same or different and independently an amino acid side-chain moiety or an amino acid side-chain derivative; and
R is a lower chain alkyl, aryl or arylalkyl moiety.

8. A method of preventing or treating inflammatory diseases, comprising administering to an animal an effective amount of a compound having the following structure:

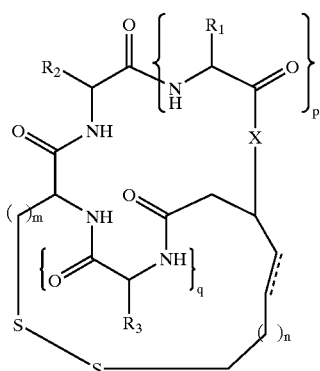
(I)

or a pharmaceutically acceptable salt or stereoisomer thereof, wherein
m is 1, 2, 3 or 4;
n is 0, 1, 2 or 3;
p and q are independently 1 or 2;
X is O, NH or NR;
$R_1$, $R_2$ and $R_3$ are the same or different and independently an amino acid side-chain moiety or an amino acid side-chain derivative; and
R is a lower chain alkyl, aryl or arylalkyl moiety.

9. A method of treating a hyperproliferative skin disease, comprising administering to an animal an effective amount of a compound having the following structure:

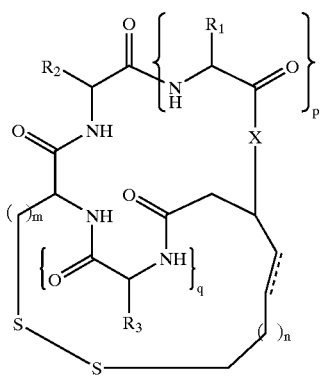
(I)

or a pharmaceutically acceptable salt or stereoisomer thereof, wherein
m is 1, 2, 3 or 4;
n is 0, 1, 2 or 3;
p and q are independently 1 or 2;
X is O, NH or NR;
$R_1$, $R_2$ and $R_3$ are the same or different and independently an amino acid side-chain moiety or an amino acid side-chain derivative; and
R is a lower chain alkyl, aryl or arylalkyl moiety.

10. A method of inhibiting the growth of CD4 T-cells and inducing apoptosis therein, comprising administering to an animal an effective amount of a compound having the following structure:

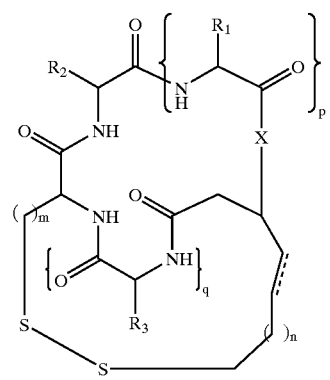
(I)

or a pharmaceutically acceptable salt or stereoisomer thereof, wherein
m is 1, 2, 3 or 4;
n is 0, 1, 2 or 3;
p and q are independently 1 or 2;
X is O, NH or NR;
$R_1$, $R_2$ and $R_3$ are the same or different and independently an amino acid side-chain moiety or an amino acid side-chain derivative; and
R is a lower chain alkyl, aryl or arylalkyl moiety.

11. A method of inhibiting the growth of CD8 T-cells and inducing apoptosis therein, comprising administering to an animal an effective amount of a compound having the following structure:

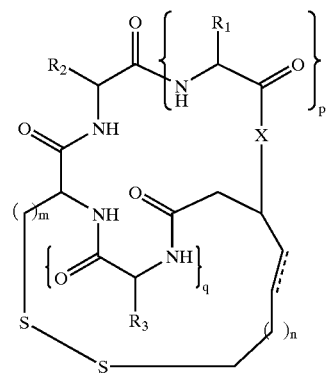
(I)

or a pharmaceutically acceptable salt or stereoisomer thereof, wherein
m is 1, 2, 3 or 4;
n is 0, 1, 2 or 3;
p and q are independently 1 or 2;
X is O, NH or NR;
$R_1$, $R_2$ and $R_3$ are the same or different and independently an amino acid side-chain moiety or an amino acid side-chain derivative; and
R is a lower chain alkyl, aryl or arylalkyl moiety.

12. A method of inhibiting c-myc expression in activated T-cells, comprising administering to an animal an effective amount of a compound having the following structure:

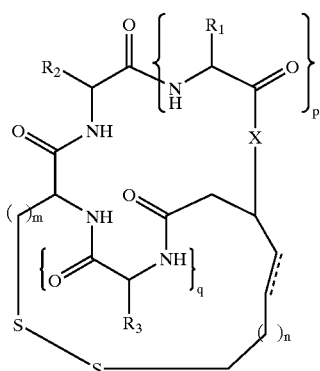
(I)
or a pharmaceutically acceptable salt or stereoisomer thereof,
wherein
m is 1, 2, 3 or 4;
n is 0, 1, 2 or 3;
p and q are independently 1 or 2;
X is O, NH or NR;
$R_1$, $R_2$ and $R_3$ are the same or different and independently an amino acid side-chain moiety or an amino acid side-chain derivative; and
R is a lower chain alkyl, aryl or arylalkyl moiety.
* * * * *